US00RE36617E

United States Patent [19]

Edwards et al.

[11] E Patent Number: Re. 36,617

[45] Reissued Date of Patent: Mar. 14, 2000

[54] (SUBSTITUTED ARALKYL) HETEROCYCLIC COMPOUNDS

[75] Inventors: Philip N. Edwards, Bramhall; Michael S. Large, Stoke-on-Trent, both of United Kingdom

[73] Assignee: Zeneca Limited, London, United Kingdom

[21] Appl. No.: 08/627,311

[22] Filed: Apr. 3, 1996

Related U.S. Patent Documents

Reissue of:

[64] Patent No.: 4,935,437
Issued: Jun. 19, 1990
Appl. No.: 07/204,743
Filed: Jun. 10, 1988

[30] Foreign Application Priority Data

Jun. 16, 1987 [GB] United Kingdom ..... 8714013

[51] Int. Cl.[7] ..... A61K 31/41; C07D 249/08

[52] U.S. Cl. ..... 514/383; 514/236.2; 514/326; 514/422; 544/132; 546/210; 548/262.2; 548/518; 548/267.4

[58] Field of Search ..... 514/383; 548/267.4

[56] References Cited

U.S. PATENT DOCUMENTS

| | | | |
|---|---|---|---|
| 4,226,878 | 10/1980 | Iizuka et al. | 548/335 |
| 4,271,170 | 6/1981 | Tanouchi et al. | 546/284 |
| 4,713,387 | 12/1987 | Watanabe et al. | 514/332 |
| 4,749,713 | 6/1988 | Bowman et al. | 514/341 |
| 4,755,526 | 7/1988 | Hirsch et al. | 514/399 |
| 4,772,623 | 9/1988 | Timmler et al. . | |
| 4,776,877 | 10/1988 | Timmler et al. . | |
| 4,912,122 | 3/1990 | Timmler et al. . | |
| 5,405,860 | 4/1995 | Timmler et al. . | |

FOREIGN PATENT DOCUMENTS 165778 12/1985 European Pat. Off. .

OTHER PUBLICATIONS

Iizuka et al, J. Med Chem., 1981, 24, 1139–1148.

Tanouchi et al., J. Med Chem., 1981, 24, 1149–1155.

Chem. Abstr., 99, 139652b, Mitsubishi Chemical.

J. Org. Chem., 1987, 52(5), 946–8 (eq. to Chem. Abstr., 106, 102640).

Chem. Abstr., 106, 50050u (1987).

Chem. Abstr., 107, (21), Nov. 23, 1987, Columbus, Ohio, U.S.A., Wickings et al, "Non–Steroidal Inhibition of Granulosa Cell Aromatase Activity in Vitro", p. 88, col. 2, Abstract No. 191 136j.

*Primary Examiner*—Patricia L. Morris

*Attorney, Agent, or Firm*—Cushman Darby & Cushman Intellectual Property Group of Pillsbury Madison & Sutro, LLP

[57] ABSTRACT

A (substituted-aralkyl)heterocyclic compound of the formula I

I

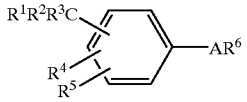

wherein $R^1$ is an azido, carbamoyl, cyano, formyl, hydroxy or nitro radical, a 1–6C 1-hydroxyalkyl, alkoxy, alkylcarbamoyl, alkylthio, alkylsulphinyl or alkylsulphonyl radical, a 2-cyanoethyl radical, optionally bearing one to four 1–6C alkyl substituents, or a 2–6C alkanoyl, halogenoalkanoyl, alkanoyloxy, alkanoylamino, dialkylcarbamoyl or alkoxycarbonyl radical; $R^2$ and $R^3$, which may be the same or different, are each a hydrogen atom, a 1–6C alkyl, dueterioalkyl or halogenoalkyl radical, or a phenyl or phenyl(1–6C alkyl) radical, in each of which the phenyl may optionally bear one or more substituents; or $R^2$ and $R^3$, together with the carbon atom to which they are attached, may form a 3- to 6-membered ring; or $R^1R^2R^3C$- is a 1,1-dicyanoethyl or trifluoromethylsulphonyl radical; $R^4$ is a hydrogen or halogen atom, a cyano or nitro radical or a 1–6C alkyl or halogenoalkyl radical; $R^5$ has any of the values defined above for the group $R^1R^2R^3C$ but is not necessarily the same as $R^1R^2R^3C$, or has any of the values defined above for $R^4$ but is not necesarily the same as $R^4$, or is a carbamoyl, 1-pyrrolidinyl-carbonyl, piperidinocarbonyl, morpholinocarbonyl or nitro radical, a 1–6C alkoxy or halogenoalkoxy radical or a 2–6C alkanoyl or alkoxy-carbonyl radical; A is a methylene or ethylene radical optionally bearing one or more substituents selected from deuterium and halogen atoms, carbamoyl, cyano and hydroxy radicals, 1–6C alkyl and alkoxy radicals, and 2–6C alkanoyloxy radicals provided that when A is linked to $R^6$ through a nitrogen atom thereof, it may not bear a hydroxy, alkoxy or alkanoyloxy substituent on the carbon atom adjacent to such nitrogen atoms; and $R^6$ is a 1H-1,2,4-triazol-1-yl, 4H-1,2,4-triazol-4-yl, 1H-imidazol-1-yl, 5-cyano-1H-imidazol-1-yl, 3-pyridyl or 5-pyrimidinyl radical, or a 1H-imidazol-1-yl radical, bearing at the 5-position thereof a 1–6C alkyl substituent which is itself optionally substituted by one or more carbamoyl, cyano, hydroxy or 2–6C alkoxycarbonyl radicals; and provided that when $R^2$, $R^3$, $R^4$ and $R^5$ are hydrogen, A is a methylene radical and $R^6$ is a 3-pyridyl radical, $R^1$ is not a cyano, hydroxy or hydroxymethyl radical, and when $R^1$ is a hydroxy radical, $R^3$, $R^4$ and $R^5$ are hydrogen, A is a methylene radical and $R^6$ is 3-pyridyl, $R^2$ is not a methyl or a 2-chloro-1-methylethyl radical, and provided that when $R^1$ is a methoxycarbonyl radical, $R^2$, $R^3$, $R^4$ and $R^5$ are hydrogen and A is a methylene radical, $R_1$ is not a 1H-imidazol-1-yl radical; and the pharmaceutically acceptable acid addition salts thereof.

10 Claims, No Drawings

(SUBSTITUTED ARALKYL) HETEROCYCLIC COMPOUNDS

Matter enclosed in heavy brackets [ ] appears in the original patent but forms no part of this reissue specification; matter printed in italics indicates the additions made by reissue.

This invention relates to (substituted-aralkyl) heterocyclic compounds, and in particular relates to such compounds which are useful as inhibitors of the enzyme aromatase.

Aromatase is an enzyme which effects aromatisation of ring A in the metabolic formation of various steroid hormones. Various cancers, for example breast cancer, are dependent upon circulating steroid hormones which have an aromatic ring A. Such cancers can be treated by removing the source of ring A aromatised steroid hormones, for example by the combination of oophorectomy and adrenalectomy. An alternative way of obtaining the same effect is by administering a chemical compound which inhibits the aromatisation of the steroid ring A, and the compounds of the invention are useful for this purpose.

A variety of compounds possessing aromatase inhibitory activity is known, of which the most important clinically is aminoglutethimide. Aminoglutethimide, however, has the drawback that it affects other aspects of steroid metabolism, with the consequence that its use is often associated with undesirable side-effects. It is a particular object of the present invention to provide aromatase inhibitory compounds with fewer undesirable side effects than aminoglutethimide.

According to the invention, there is provided a (substituted-aralkyl)heterocyclic compound of the formula I wherein $R^1$ is an azido, carbamoyl, cyano, formyl, hydroxy or nitro radical, a 1–6C 1-hydroxyalkyl, alkoxy, alkylcarbamoyl, alkylthio, alkylsulphinyl or alkylsulphonyl radical, a 2 cyanoethyl radical, optionally bearing one to four 1–6C alkyl substituents, or a 2–6C alkanoyl, halogenoalkanoyl, alkanoyloxy, alkanoylamino, dialkylcarbamoyl or alkoxycarbonyl radical; $R^2$ and $R^3$, which may be the same or different, are each a hydrogen atom, a 1–6C alkyl, deuterioalkyl or halogenoalkyl radical, or a phenyl or phenyl(1–6C alkyl) radical, in each of which the phenyl may optionally bear one or more substituents; or $R^2$ and $R^3$, together with the carbon atom to which they are attached, may form a 3- to 6-membered ring; or $R^1R^2R^3C$— is a 1,1-dicyanoethyl or trifluoromethylsulphonyl radical; $R^4$ is a hydrogen or halogen atom, a cyano or nitro radical or a 1–6C alkyl or halogenoalkyl radical; $R^5$ has any of the values defined above for the group $R^1R^2R^3C$ but is not necessarily the same as $R^1R^2R^3C$, or has any of the values defined above for $R^4$ but is not necessarily the same as $R^4$, or is a carbamoyl, 1-pyrrolidinylcarbonyl, piperidinocarbonyl, morpholinocarbonyl or nitro radical, a 1–6C alkoxy or halogenoalkoxy radical or a 2–6C alkanoyl or alkoxycarbonyl radical; A is a methylene or ethylene radical optionally bearing one or more substituents selected from deuterium and halogen atoms, carbamoyl, cyano and hydroxy radicals, 1–6C alkyl and alkoxy radicals, and 2–6C alkanoyloxy radicals provided that when A is linked to $R^6$ through a nitrogen atom thereof, it may not bear a hydroxy, alkoxy or alkanoyloxy substituent on the carbon atom adjacent to such nitrogen atoms; and $R^6$ is a 1H-1,2,4-triazol-1-yl, 4 H-1,2,4-triazol-4-yl, 1H-imidazol-1-yl, 5 cyano-1 H-imidazol-1-yl, 3-pyridyl or 5-pyrimidinyl radical, or a 1 H-imidazol-1-yl radical, bearing at the 5-position thereof a 1–6C alkyl substituent which is itself optionally substituted by one or more carbamoyl, cyano, hydroxy or 2–6C alkoxycarbonyl radicals; and provided that when $R^2$, $R^3$, $R^4$ and $R^5$ are hydrogen, A is a methylene radical and $R^6$ is a 3-pyridyl radical, $R^1$ is not a cyano, hydroxy or hydroxymethyl radical, and when $R^1$ is a hydroxy radical, $R^3$, $R^4$ and $R^5$ are hydrogen, A is a methylene radical and $R^6$ is 3-pyridyl, $R^2$ is not a methyl or a 2-chloro-1-methylethyl radical, and provided that when $R^1$ is a methoxycarbonyl radical, $R^2$, $R^3$, $R^4$ and $R^5$ are hydrogen and A is a methylene radical, $R^1$ is not a 1H-imidazol-1-yl radical; and the pharmaceutically acceptable acid addition salts thereof.

A suitable value for $R^1$ when it is a hydroxyalkyl radical, or for a hydroxyalkyl radical in $R^5$ when it is a group of the formula $R^1R^2R^3C$ is, for example, a hydroxymethyl, 1-hydroxyethyl, 1-hydroxy-1-methylethyl, 1-hydroxypropyl, 1-hydroxy-1-methylpropyl, 1-hydroxy-2-methylpropyl, 1-hydroxybutyl, 1-hydroxypentyl or 1-hydroxyhexyl radical.

A suitable value for $R^1$ or $R^5$ when either is an alkoxy radical, or for an alkoxy radical in $R^5$ when it is a group of the formula $R^1R^2R^3C$, or for an optional alkoxy substituent in A, is, for example, a methoxy, ethoxy, propoxy, isopropoxy, butoxy, isobutoxy, sec-butoxy, tert-butoxy, pentyloxy, neopentyloxy or hexyloxy radical.

A suitable value for $R^1$ when it is an alkylthio radical, or for an alkylthio radical in $R^5$ when it is a group of the formula $R^1R^2R^3C$, is, for example, a methylthio, ethylthio, propylthio, isopropylthio, butylthio, isobutylthio, sec-butylthio, tert-butylthio, pentylthio, neopentylthio or hexylthio radical.

A suitable value for $R^1$ when it is an alkylsulphinyl radical, or for an alkylsulphinyl radical in $R^5$ when it is a group of the formula $R^1R^2R^3C$, is, for example, a methylsulphinyl, ethylsulphinyl, propylsulphinyl, isopropylsulphinyl, butylsulphinyl, isobutylsulphinyl, sec-butylsulphinyl, tert-butylsulphinyl, pentylsulphinyl, neopentylsulphinyl or hexylsulphinyl radical.

A suitable value for $R^1$ when it is an alkylsulphonyl radical, or for an alkylsulphonyl radical in $R^5$ when it is a group of the formula $R^1R^2R^3C$, is, for example, a methylsulphonyl, ethylsulphonyl, propylsulphonyl, isopropylsulphonyl, butylsulphonyl, isobutylsulphonyl, sec-butylsulphonyl, tert-butylsulphonyl, pentylsulphonyl, neopentylsulphonyl or hexylsulphonyl radical.

A suitable value for $R^1$ or $R^5$, when either is an alkanoyl radical, or for an alkanoyl radical in $R^5$ when it is a group of the formula $R^1R^2R^3C$, is, for example, an acetyl, butyryl, isobutyryl, valeryl, isovaleryl, pivaloyl or hexanoyl radical.

A suitable value for $R^1$ when it is a halogenoalkanoyl radical, or for a halogenoalkanoyl radical in $R^5$ when it is a group of the formula $R^1R^2R^3C$, is, for example, a chloroacetyl, dichloroacetyl, trichloroacetyl, trifluoroacetyl, 2,2,2-trichloropropionyl, 2,2,2-trifluoropropionyl, 1,2,2-trifluoropropionyl, 1,2,2,2-tetrafluoropropionyl, perfluoropropionyl, 2,2,3,3,3-pentafluorobutyryl, 2,2-dichloro-3,3,3-trifluorobutyryl, 4,4,4-trifluorovaleryl or 5,5,5-trifluorohexanoyl radical.

A suitable value for $R^1$ when it is an alkanoyloxy radical, or for an alkanoyloxy radical in $R^5$ when it is a group of the formula $R^1R^2R^3C$, or for an optional alkanoyloxy substituent in A, is, for example, an acetoxy, propionyloxy, butyryloxy, isobutyryloxy, valeryloxy, isovaleryloxy, pivaloyloxy or hexanoyloxy radical.

A suitable value for $R^1$ when it is an alkanoylamino radical, or for an alkanoylamino radical in $R^5$ when it is a group of the formula $R^1R^2R^3$, is, for example, an acetamido, propionamido, butyramido, isobutyramido, valeramido, isovaleramido, pivalamido or hexanamido radical.

A suitable value for $R^1$ or $R^5$, when either is an alkoxycarbonyl radical, or for an alkoxycarbonyl radical in $R^5$ when it is a group of the formula $R^1R^2R^3C$, is, for example, a methoxycarbonyl, ethoxycaronyl, propoxycarbonyl, isopropoxycarbonyl, butoxycarbonyl, isobutoxycarbonyl, sec-butoxycarbonyl, tert-butoxycarbonyl or pentyloxycarbonyl radical.

A suitable value for $R^2$, $R^3$ or $R^4$, when any is an alkyl radical, or for an optional alkyl substituent in A, is, for example a methyl, ethyl, propyl, isopropyl, butyl, isobutyl, sec-butyl, tert-butyl, pentyl, neopentyl or hexyl radical.

A suitable value for $R^2$ or $R^3$, when either is a deuterioalkyl radical, is, for example, a trideuteriomethyl radical.

A suitable value for $R^2$, $R^3$ or $R^4$, when any is a halogenoalkyl radical, is, for example, a mono-, di- or tri-chloromethyl, mono-, di- or trifluoromethyl, 2,2,2-trichloro- or trifluoro-ethyl, 1,2,2-trichloro-or trifluoroethyl, pentafluoroethyl, 2,2,3,3,3-pentafluoropropyl, 2,2-dichloro-3,3,3-trifluoropropyl, 4,4,4-trifluorobutyl, 5,5,5-trifluoropentyl or 6,6,6-trifluorohexyl radical.

When either of $R^2$ and $R^3$ is a substituted phenyl or phenyl(1–6C)alkyl) radical, the phenyl may bear one to five, preferably one or two, substituents selected from halogen atoms, for example fluorine, chlorine and bromine atoms, and cyano and 1–6C alkyl radicals. A suitable phenyl(1–6C) alkyl) radical is, for example, a benzyl, phenethyl, 1-phenylethyl or 1-methyl-1-phenylethyl radical.

A suitable value for $R^4$ when it is a halogen atom is, for example, a fluorine, chlorine, bromine or iodine atom.

A suitable value for $R^5$ when it is a halogenoalkoxy radical is, for example, a mono-, di- or tri-chloromethoxy, mono-, di- or tri-fluoromethoxy, bromomethoxy, iodomethoxy, 2,2,2-trichloro- or trifluoro-ethoxy, 1,2,2-trichloro- or trifluoro-ethoxy, pentafluoroethoxy, 2,2,3,3,3-pentafluoropropoxy, 2,2-dichloro-3,3,3-trifluoropropoxy, 4,4,4-trifluorobutoxy, 5,5,5-trifluoropentyloxy or 6,6,6-trifluorohexyloxy radical.

Suitable values for A, when it is a substituted methylene or ethylene radical are, for example, an ethylidene, propylidene, butylidene, 1- or 2-methylethylene, 1,2-dimethylethylene, dideuteriomethylene, difluoromethylene, hydroxymethylene, cyanomethylene, carbamoylmethylene and 1-hydroxyethylene (in which C-1 of the ethylene is linked to the benzene ring) radicals.

Suitable pharmaceutically acceptable acid addition salts are, for example, hydrochlorides, hydrobromides, sulphates, nitrates, phosphates and toluene-p-sulphonates.

It is to be understood that when A bears one or more substituents as defined above, one or both of the carbon atoms in A may be asymmetrically substituted, and that the carbon atom bearing substituents $R^1$, $R^2$ and $R^3$ may also be asymmetrically substituted, so that the compounds of the invention may exist in racemic or optically active forms. It is common general knowledge how such optically active and meso forms may be synthesized or separated, and their respective aromatase inhibitory properties determined.

A preferred group of compounds of the invention comprises compounds wherein $R^1$ is a cyano radical, $R^5$ is a radical of the formula $R^1R^2R^3C$ wherein $R^1$ is a cyano or hydroxy radical, and $R^6$ is a 1H-imidazol-1-yl or 1 H-1,2,4-triazol-1-yl radical, and especially preferred are such compounds wherein $R^2$ and $R^3$, both in the group $R^1R^2R^3C$ and in $R^5$, are methyl or trideuteriomethyl radicals and A is a methylene or dideuteriomethylene radical.

Particular preferred compounds are the compounds described below as Examples 1, 9, 33, 53 and 54, that is respectively 2,2'-[5-(1H-1,2,4-triazol-1-ylmethyl)-1,3-phenylene]di(2-methylpropiononitrile), 2,2'-[5-(imidazol-1-ylmethyl)-1,3-phenylene]di(2-methylpropiononitrile), 2-[3-(1-hydroxy-1-methylethyl)-5-(1H-1,2,4-triazol-1-ylmethyl)phenyl]-2 methylpropiononitrile, 2,2'-[5-dideuterio-(1H-1,2,4-triazol-1-yl)methyl-1,3-phenylene]di(2-trideuteriomethyl-3,3,3-trideuteriopropiononitrile) and 2,2'-[5-dideuterio(1H-1,2,4-triazol-1-yl)methyl-1,3-phenylene]di(2-methylpropiononitrile).

The compounds of the invention may be manufactured by processes known per se for the manufacture of analogous compounds. Thus, the following processes are provided as further features of this invention, in which $R^1$, $R^2$, $R^3$, $R^4$, $R^5$, $R^6$ and A have the meanings defined above, unless otherwise stated:

(a) the reaction of a compound of the formula II, wherein X is a known displaceable leaving group, with a heterocyclic compound of the formula $R^6$ H, or with a reactive metal derivative thereof, or with a protected derivative thereof wherein a nitrogen atom which is intended not to be involved in the reaction with the compound of the formula II is protected by a known nitrogen protecting group, whereafter the said protecting group is removed; or (b) for those compounds wherein A is a hydroxymethylene radical or an optionally-substituted 2-hydroxyethylene radical, in which C-1 of the ethyl radical is attached to the benzene ring, the reaction of an oxo compound of the formula III wherein Al is a direct bond or a methylene radical, optionally substituted as defined above and $R^7$ is one of the optional substituents in A defined above, with an alkali metal derivative of a heterocyclic compound of the formula $R^6$ H; or (c) for those compounds wherein A is a 1-hydroxyethylene radical, in which 0–1 of the ethylene radical is attached to the benzene ring, the reaction of an epoxide of the formula IV, either as such or formed in situ in the reaction, with a heterocyclic compound of the formula $R^6$ H; or (d) for those compounds wherein $R^6$ is a 5-cyanoimidazol-1-yl radical, the reaction of the corresponding 5-oximino-imidazol-1-yl compound with a dehydrating agent; whereafter if desired (i) a compound of the invention in which $R^1$, $R^4$ or $R^5$ is a cyano radical is hydrolysed with an acid to form a compound of the invention bearing a corresponding carbamoyl substituent; or (ii) a compound of the invention in which $R^1$ or $R^5$ is an alkoxycarbonyl radical is reacted with ammonia, pyrrolidine, piperidine or morpholine to form a compound of the invention wherein $R^1$ or $R^5$ is a corresponding carbamoyl substituent, or $R^5$ is a corresponding 1-pyrrolidinylcarbonyl, piperidinocarbonyl or morpholinocarbonyl substituent; or (iii) a compound of the invention in which $R^1$ or $R^5$ is a carbamoyl radical is dehydrated with an acid anhydride to form a compound of the invention bearing a corresponding cyano substituent; or (iv) a compound of the invention in which $R^1$ or $R^5$ is an alkoxycarbonyl substituent is reduced to form a compound of the invention bearing a corresponding hydroxymethyl substituent; or (v) a compound of the invention in which $R^4$ or $R^5$ is a hydroxyalkyl radical is reacted with a halogenating agent to form a compound of the invention in which $R^4$ or $R^5$ is a corresponding halogenoalkyl substituent; or (vi) a compound of the invention in which $R^5$ is a halogenoalkyl substituent is reacted with an alkali metal cyanide to form a compound of the invention wherein $R^5$ is a group of the formula $R^1R^2R^3$ which is a cyanoalkyl substituent; or (vii) a compound of the invention in which $R^5$ is a halogenoalkyl radical is reacted with an alkali metal alkylthiolate to form a compound of the invention wherein $R^5$ is a group $R^1R^2R^3C$ in which $R^1$ is an alkylthio substituent; or (viii) a compound of the invention in which $R^5$ is a group $R^1R^2R^3C$ wherein, $R^1$ is an alkylthio radical is reacted with an oxidising agent to form a compound of the invention in which $R^5$ is a group $R^1R^2R^3C$ wherein $R^1$ is an alkylsulphinyl or alkylsulphonyl radical; or (ix) a compound of the invention in which $R^1$ or $R^5$ is an alkoxycarbonyl radical is reacted with an alkylmagnesium halide to form a compound of the invention in which $R^1$ or $R^5$ is a corresponding hydroxyalkyl radical; or (x) a compound of the invention in which A bears a hydroxy substituent is reacted with a halogenating agent to form a corresponding compound of the invention in which A bears a halogen substituent; or (xi) a compound of the invention in which A bears a halogen substituent is hydrogenated to form a corresponding compound of the invention wherein A lacks the halogen substituent of the starting compound; or (xii) a compound of the invention in which $R^1$ is a 1-hydroxyalkyl radical wherein C-1 bears a hydrogen atom, is oxidised to form a compound of the invention wherein $R^1$ is an alkanoyl radical; or (xiii) a compound of the invention in which A is a 1-hydroxyethylene radical wherein C-1 of the ethylene radical is attached to the benzene ring, is converted to a compound of the invention in which A is an ethylene radical by successively reacting with a halogenating agent to form the corresponding 1-halogenoethylene compound, dehydrohalogenating the 1-halogenoethylene compound to the corresponding compound in which A is vinylene, and hydrogenating the compound in which A is vinylene; or (xiv) a compound of the invention in which $R^1$ is a 2–6C alkanoyl radical is reduced to form a compound of the invention wherein $R^1$ is a 1-hydroxyalkyl radical: or (xv) a compound of the invention in which $R^1$ is a hydroxy radical is reacted with a trialkylsilane to form a compound of the invention wherein $R^4$ is an alkyl radical; or (xvi) a compound of the invention in which $R^4$ is a halogen atom is reacted with a metal cyanide to form a compound of the invention wherein $R^4$ is a cyano radical.

In process (a), a suitable value for the known displaceable leaving group X is, for example, a halogen atom, for example a chlorine or bromine atom, or an alkylsulphonyloxy or arylsulphonyloxy radical, for example a mesyloxy or tosyloxy radical or a hydroxy radical. When X is a hydroxy radical, the process is preferably carried out in trifluoroacetic acid. A suitable metal derivative of a heterocyclic compound of the formula $R^6$ H is an alkali metal derivative, such as sodium 1H-1,2,4-triazole or 3-pyridyl-lithium A suitable known nitrogen protecting group for a nitrogen atom of $R^6$ H which is intended not to be involved in the reaction with the compound of the formula II is, for example, a trityl radical. Such a trityl protecting group can be readily removed by acid treatment. Examples of the use of such a protected heterocyclic compound are Examples 5 and 6 hereafter, in which $R^6$H is 4-methyl-1-tritylimidazole, leading to the desired 5-methyl-1-imidazolyl products rather than the undesired 4-methyl-1-imidazolyl isomers.

The compound of the formula II wherein X is a bromine atom, which is used as starting material in process (a), may be obtained by standard, relatively simple processes involving bromination of an appropriately-substituted alkylbenzene. For example, 3,5-bis(bromomethyl)toluene V was reacted with potassium cyanide to form 3,5-bis(cyanomethyl)toluene VI, which was then alkylated with an iodoalkane $R^2$I or $R^3$I to form VII, which in turn was brominated with N bromosuccinimide to form the required starting material II, X=Br.

Similarly, starting materials of the formula II wherein X is chlorine, alkylsulphonyloxy or arylsulphonyloxy may be obtained by conventional procedures. For example, methyl 3,5-dimethylbenzoate VIII was brominated with N bromosuccinimide to form the 3,5-bis(bromomethyl) compound IX, which was converted as described above to the corresponding dinitrile X and alkylated dinitrile XI. This compound XI was then reduced, for example with lithium borohydride, to the corresponding alcohol XII, which was then converted either to the starting material of the formula II in which X is chlorine by reaction with thionyl chloride or phosphoryl chloride, or to a starting material of the formula II in which X is an alkylsulphonyloxy or arylsulphonyloxy radical by reaction with an appropriate alkylsulphonyl chloride or arylsulphonyl chloride, for example mesyl chloride or tosyl chloride. Starting materials of the formula II bearing other of the defined substituents may be obtained by generally similar processes.

Starting materials of the formula II wherein X is a hydroxy radical may similarly be made by conventional procedures, for example as described above for a compound of the formula XII. Corresponding starting materials wherein A is an alkylated methylene group may be obtained by reacting a methoxycarbonyl compound, such as for example compound XI, with a Grignard reagent, for example methylmagnesium chloride.

In process (b), suitable alkali metal derivatives of a heterocyclic compound of the formula $R^6$ H are those described above, under process (a).

The oxo compound of the formula III used as starting material in process (b) may be obtained by oxidation of the corresponding hydroxyalkyl compound, (for example compound XIII), for example with pyridinium chlorochromate The epoxide of the formula IV, used in process (c), may be obtained by reacting an aldehyde of the formula III with trimethylsulphoxonium iodide in the presence of a base, for example potassium hydroxide. The epoxide may be isolated as such, and then reacted with a heterocyclic compound $R^6$H, or the epoxide may be formed in situ by reacting the aldehyde of the formula III, trimethylsulphoxonium iodide and the heterocyclic compound $R^6$H together in one reaction.

In process (d), a suitable dehydrating agent is, for example, trifluoroacetic anhydride.

In optional process (i), a suitable acid for use in the hydrolysis process is, for example, hydrochloric acid or sulphuric acid.

In optional process (iii), a suitable acid anhydride is, for example, trifluoroacetic anhydride.

The reduction in optional process (iv) may be carried out with, for example, a metal hydride reducing agent, for example lithium aluminium hydride or lithium borohydride.

A suitable halogenating agent for use in optional processes (v), (x) and (xiii) is, for example, thionyl chloride or phosphoryl chloride.

In process (vi), a suitable alkali metal cyanide is, for example, potassium cyanide or sodium cyanide.

The oxidation in optional process (viii) may be carried out using, for example, a derivative of a peracid, for example sodium periodate, peracetic acid or m-chloroperbenzoic acid.

In optional process (x), a suitable halogenating agent to obtain fluorine-substituted compound of the invention is, for example, diethylaminosulphur trifluoride In optional process (xi), the hydrogenation may be carried out over a metal catalyst, for example, palladium, platinum or nickel, at normal temperature and pressure The oxidation in optional process (xii) may be carried out, for example, with dimethylsulphoxide and oxalyl chloride, Jones's reagent or periodinane.

In optional process (xiii), the dehydrohalogenation reaction may be carried out with a base, for example, sodium triazole, a sodium (lower alkoxide) or sodium hydroxide.

In optional process (xiv), a suitable reducing agent is, for example, sodium borohydride.

In optional process (xv), a suitable trialkylsilane is, for example, triethylsilane, in trifluoroacetic acid.

In optional process (xvi), a suitable halogen substituent is, for example, a bromine atom, and a suitable metal cyanide is, for example, cuprous cyanide.

The processes (a) to (d) of the invention, and optional subsequent processes (i) to (xiii) may be carried out as specified, and may be accelerated or completed by heating.

As indicated above, the compounds of the invention of the formula I are useful as aromatase inhibitors. Aromatase inhibition may be demonstrated by the following tests:

DEMONSTRATION OF ACTIVITY IN VITRO

Aromatase inhibitory activity was measured using the enzyme present in the microsomal fraction of human term placenta, as described by Ryan, J. Biol, Chem. 234,268, 1959. Enzyme activity was determined by measuring the amount of tritiated water released from 0.5 micromolar (1β,2β-$^3$H)testosterone after 20 minutes incubation at 37°. The method used was essentially that described by Thomson and Siiteri, J. Biol. Chem. 249,5364,1974 except that testosterone was used in place of androstenedione Test compounds were dissolved in dimethylsulphoxide (DMSO) then diluted as appropriate to achieve final concentrations of 2, 0.2 or 0.02 μg/ml. The reaction was started by the addition of 50 μl of microsome suspension to 50 μl of a solution containing substrate (testosterone) and cofactors (NADPH glucose-6-phosphate and glucose-6-phosphate dehydrogenase) and either DMSO alone or a DMSO solution of test compound Each concentration of test compound was tested in triplicate. The reaction was stopped by the addition of 200 μl of 5% (w/v) suspension of charcoal in 0.5% (w/v) solution of Dextran T70 in water. After 1 hour the charcoal was precipitated by centrifugation and 150 μl of supernatant removed and the amount of tritiated water present determined using a liquid scintillation counter. The number of counts in supernatant from incubations containing test compound expressed as a percentage of the counts in supernatant from incubations containing only DMSO was taken as the degree of enzyme inhibition achieved by the test compound

DEMONSTRATION OF ACTIVITY IN VIVO

Activity in vivo was demonstrated in terms of ovulation inhibition in female rats. Daily vaginal smears were taken from rats housed under controlled lighting (lights on 06.00 hr to 20.00 hr) and those having a vaginal smear pattern consistent with 4 day ovarian cycles were selected To these rats a single dose of test compound was given either at 16.00 hr on Day 2 of the cycle or at 12.00 hr on Day 3 of the cycle. The rats were then killed in the morning following Day 4 of the cycle—approximately 64 hours after Day 2 treatments or approximately 46 hours after Day 3 treatments—and the presence or absence of eggs in the fallopian tubes determined. The presence of eggs indicates that the rats have ovulated.

Without treatment more than 95% of rats with 4-day ovarian cycles are found to have ovulated at the time of the post-mortem examination. At an effective dose, aromatase inhibitors prevent ovulation i.e. no eggs are found in the fallopian tubes.

In the above tests, the compounds of formula I are active at less than 10 μg/ml (in vitro), and the preferred compounds of the formula I are active at below 0.1 μg/ml (in vitro) and 1.0 mg/kg (in vivo), and no indication of any toxicity has been seen at these doses.

Thus, according to a further feature of the invention there is provided a pharmaceutical or veterinary composition which comprises an effective amount of a compound of the formula I together with a pharmaceutically or veterinarily acceptable diluent or carrier.

The composition of the invention may be in a conventional pharmaceutical form suitable for oral administration, for example a tablet, a capsule, an emulsion or an aqueous or oily solution or suspension. The composition may contain conventional pharmaceutical excipients, and may be manufactured by conventional pharmaceutical techniques.

Preferred pharmaceutical or veterinary compositions of the invention are tablets and capsules containing from 0.1 to 100, preferably 0.25 to 25 mg. of a compound of the invention.

The invention is illustrated but not limited by the following Examples. Melting points are given in degrees Celsius. Flash column chromatography was carried out on silica gel (Merck Kieselgel 60H).

EXAMPLE 1

A mixture of 2,2'-(5-methyl-1,3-phenylene)di(2-methylpropiononitrile), (2.26 g), N-bromosuccinimide (1.78 g), benzoyl peroxide (0.05 g) and carbon tetrachloride (50 ml) was heated under reflux for 2 h, cooled and filtered, and the filtrate was evaporated to dryness under reduced pressure. The residue was dissolved in dimethylformamide (20 ml), sodium triazole (1.8 g) was added, and the mixture was stirred at room temperature for 18 h. Water (100 ml) was added, and the mixture was extracted twice with ethyl acetate. The extracts were combined, dried and evaporated to dryness under reduced pressure, and the residue was purified by flash column chromatography, eluting with ethyl acetate, to give 2,2'-[5-(1H-1,2,4-triazol-1-ylmethyl)-1,3-phenylene]di(2-methylpropiononit rile), mp 81°–82° after crystallisation from ethyl acetate/cyclohexane.

The 5-methyl-1,3-phenylene compound used as starting material in the above process may be prepared as follows:

A mixture of 3,5-bis(bromomethyl)toluene (30 g), tetrabutylammonium bromide (1 g), potassium cyanide (17.6 g), dichloromethane (100 ml) and water (30 ml) was stirred vigorously and heated under reflux for 3 h. The mixture was cooled, diluted with water (100 ml) and extracted three times with ethyl acetate. The extracts were combined, dried and evaporated to dryness, and the residue was purified by flash column chromatography, eluting with petroleum ether (bp 60°–80°): ethyl acetate (3:1 by volume), to give 2,2'-(5-methyl-1,3-phenylene)diacetonitrile, mp 73 74° after crystallisation from carbon tetrachloride.

A mixture of this diacetonitrile (11.5 g), iodomethane (42 g) and dimethylformamide (150 ml) was cooled in an ice bath and stirred while sodium hydride (50% dispersion in mineral oil, 15 g) was added in portions over 1 h. The mixture was then allowed to warm to room temperature and stirred for 2 h, then water (500 ml) was added, and the mixture was extracted twice with ethyl acetate. The extracts were combined, dried and evaporated to dryness under reduced pressure, and the residue was crystallised from carbon tetrachloride to give the required 5-methyl-1,3-phenylene starting material, mp 126°–127°.

EXAMPLES 2–4

The process described in Example 1 was repeated, using the appropriate 5-methyl-1,3-disubstituted phenylene compound as starting material, to give the following compounds:

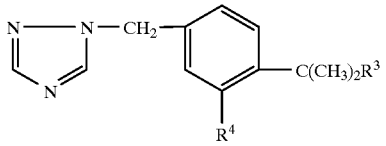

| Example | $R^3$ | $R^4$ | Mp | Footnotes |
|---|---|---|---|---|
| 2 | CN | $—C(CH_3)_2COCH_3$ | — | 1,2 |
| 3 | $COCH_3$ | $—C(CH_3)_2COCH_3$ | 73–75 | 2 |
| 4 | CN | $—COOCH_3$ | 159–161 | 3,4 |

Footnotes

1. Nmr in deuteriochloroform; δ 8.12(1H, s), 8.0(1H, s), 7.35(1H, m), 7.25(1H, m), 7.1(1H, m), 5.37(2H, s), 1.92(3H, s), 1.70(6H, s), 1.48(6H, s).
2. The 2-methyl-2-[5-(1,1-dimethyl-2-oxopropyl)-3-tolyl]propiononitrile required as starting material for Example 2 and the 1,1'-(5-methyl-1,3-phenylene)di(1,1-dimethyl-2-propanone) required as the starting material for Example 3, were obtained as follows:- A solution of methylmagnesium chloride in tetrahydrofuran (3M, 1 ml) was added to a solution of 2,2'-(5-methyl-1,3-phenylene)di(2-methylpropiononitrile) (0.45 g) in tetrahydrofuran, and heated under reflux in an atmosphere of argon for 6 h. The mixture was cooled, treated with 2N aqueous hydrochloric acid (5 ml) and stirred at room temperature for 18 h. The mixture was then extracted twice with ethyl acetate, and the combined extracts were dried and evaporated to dryness under reduced pressure. The residue was purified by flash column chromatography. Elution with dichloromethane: cyclohexane (2:1 by volume) gave the required starting material for Example 2, mp 37–39°, and subsequent elution with dichloromethane gave the required starting material for Example 3, mp 81–82°.
3. Hydrochloride salt.
4. The methyl 5-(1-cyano-1-methylethyl)-3-toluate starting material was obtained as follows:- A mixture of methyl 3,5-dimethylbenzoate (10 g), N-bromosuccinimide (11.94 g), benzoyl peroxide (0.1 g) and carbon tetrachloride (100 ml) was heated under reflux for 2 h, cooled and filtered, and the filtrate was evaporated to dryness under reduced pressure. The residue was purified by flash column chromatography, and elution with ethyl acetate:petroleum ether (bp 60–80°), (3:97 by volume) gave methyl 5-bromomethyl-3-toluate as an oil, which was then used in place of 3,5-bis(bromomethyl) toluene in the process described in the second part of Example 1 to give successively methyl 5-cyanomethyl-3-toluate, mp 56–57° after crystallisation from cyclohexane, and the required starting material, methyl 5-(1-cyano-1-methylethyl)-3-toluate, mp. 50–51° after crystallisation from hexane.

EXAMPLE 5

A mixture of methyl 3-bromomethyl-5-(1-cyano-1-methylethyl)benzoate (0.7 g), 4-methyl-1-tritylimidazole (0.8 g) and acetonitrile (2 ml) was heated under reflux for 48 h, then evaporated to dryness. The residue of 3-[3-(1-cyano-1-methylethyl)-5-methoxycarbonylbenzyl]-4-methyl-1-tritylimi dazolium bromide was washed with diethyl ether (2×10 ml), and the residue was treated with glacial acetic acid (4 ml) and water (1 ml) and heated at 90° for 15 minutes. The mixture was diluted with water (20 ml), and washed with diethyl ether, and the aqueous phase was basified with 10N aqueous sodium hdroxide and extracted three times with ethyl acetate. The extracts were combined and evaporated to dryness, and the residue was purified by flash column chromatography, eluting with methanol:chloroform (1:49 by volume), to give methyl 5-(1-cyano-1-methylethyl)-3-(5-methylimidazol-1-ylmethyl)benzoate, mp 101°–104°.

The 4-methyl-1-tritylimidazole used in the above process was prepared as follows:

A mixture of trityl chloride (17 g), triethylamine (8.5 ml), 4-methylimidazole (5 g) and toluene (40 ml) was stirred at 80° for 4 h and filtered, and the solid material was washed with toluene. It was then partitioned between water and chloroform, and the chloroform solution was separated, dried and combined with the dried toluene filtrate. The combined organic solutions were evaporated to dryness under reduced pressure, and the residue was triturated with diethyl ether to give 4-methyl-1-tritylimidazole, mp. 214°–216°.

EXAMPLE 6

The process described in Example 5 was repeated, using 2,2'-(5-bromomethyl-1,3-phenylene)di(2-methylpropiononitrile) as the starting material, to obtain 2,2'-[5-(5-methylimidazol-1-yl)-1,3-phenylene]di(2-methylpropiononitrile), mp. of hydrochloride salt, 183°–185°, crystallised from ethyl acetate.

EXAMPLE 7

A mixture of 2,2'-[5-(1-chloroethyl)-1,3-phenylene)di(2-methylpropiononitrile), (0.35 g), sodium triazole (0.25 g) and dimethylformamide (3 ml) was stirred at room temperature for 18 h, then water (20 ml) was added and the mixture was extracted twice with ethyl acetate. The extracts were combined and evaporated to dryness, and the residue was purified by flash column chromatography, eluting with ethyl acetate, to give 2,2'-[5-(1-[1H-1,2,4-triazol-1-yl]ethyl)-1,3-phenylene]di(2-methylpropiononitrile), crystallised as the hydrochloride from acetone, mp. 168°–170°.

The 5-(1-chloroethyl)-1,3-phenylene derivative used as starting material in the above process may be prepared as follows:

A solution of 2,2'-(5-hydroxymethyl-1,3-phenylene)di(2-methylpropiononitrile), (1.9 g), in dichloromethane (20 ml) was treated with pyridinium chlorochromate (2.15 g) and stirred at room temperature for 1.5 h. The reaction mixture was subjected to flash column chromatography, eluting with dichloromethane, to give 2,2'-(5-formyl-1,3-phenylene)di (2-methylpropiononitrile), mp. 145°–147°.

This compound (0.48 g) was dissolved in tetrahydrofuran (5 ml), and the solution was stirred at 0° under an atmosphere of argon while a solution of methylmagnesium chloride in tetrahydrofuran (3M, 0.7 ml) was added over 5 minutes. The mixture was stirred for 0.5 h, then a saturated aqueous solution of ammonium chloride was added, and the mixture was extracted twice with diethyl ether. The extracts were combined, dried and evaporated to dryness under reduced pressure to give 2,2'-[5-(1-hydroxyethyl)-1,3-phenylene]di(2-methylpropiononitrile), which was used without further purification. This was dissolved in dichloromethane (5 ml). and ice-cooled while pyridine (0.16 g) was added, followed by thionyl chloride (0.36 g) dropwise. The mixture was kept at room temperature for 2 h, then evaporated to dryness. The residue was partitioned between diethyl ether and water, and the ether phase was separated, dried and evaporated to dryness under reduced pressure to give the required 2,2'-[5-(1-chloroethyl)-1,3-phenylene]di (2-methylpropiononitrile), which was used without further purification.

EXAMPLE 8

A solution of 2,2'-(5-chloromethyl-1,3-phenylene)di(2-methylpropiononitrile), (0.23 g), and 1H-1,2,4-triazole (0.35 g) in acetonitrile (2 ml) was heated under reflux for 18 h, then evaporated to dryness. The residue was partitioned between 1N aqueous potassium hydrogen carbonate solution and ethyl acetate, the organic phase was separated, dried and evaporated to dryness under reduced pressure, and the residue was purified by flash column chromatography. Elution with methanol:chloroform (1:49 by volume), gave 2,2'-[5-(1H-1,2,4-triazol-1-ylmethyl)-1,3-phenylene]di(2-methylpropiononitrile), identical with the product of Example 1, and further elution with methanol:chloroform (2:23 by volume, gave 2,2'-[5-(4H-1,2,4-triazol-4-yl-methyl)-1,3-phenylene]di(2-methylpropiononitrile), mp. 158°–161°.

The chloromethyl compound used as starting material in the above process may be prepared as follows:

A mixture of methyl 3,5-dimethylbenzoate (6 g), N-bromosuccinimide (13 g), benzoyl peroxide (50 mg) and carbon tetrachloride (150 ml) was heated under reflux for 1 h. The mixture was then cooled and filtered, the filtrate was evaporated to dryness under reduced pressure, and the residue was crystallised from cyclohexane to give methyl 3,5-bis(bromomethyl)benzoate mp. 99°–101°.

The methyl 3,5-bis(bromomethyl)benzoate was treated with potassium cyanide in a similar manner to that described in the second part of Example I to give methyl 3,5-bis (cyanomethyl)benzoate mp. 90°–92°, which was then alkylated with methyl iodide as also described in the latter part of Example I, to give methyl 3,5-bis(1-cyano-1-methyl ethyl)benzoate, mp. 83°–85°.

A mixture of methyl 3,5-bis(1-cyano-1-methyl ethyl) benzoate (5.6 g), lithium borohydride (0.44 g) and tetrahydrofuran (30 ml) was heated under reflux for 2 h. The mixture was cooled and stirred while 2N aqueous hydrochloric acid was added dropwise until the solution remained acidic, and then the mixture was extracted twice with ethyl acetate. The combined extracts were washed with 1N aqueous potasium bicarbonate solution and then dried and evaporated to dryness under reduced pressure to give 2,2'-(5-hydroxymethyl-1,3-phenylene)di(2-methylpropiononitrile), mp. 151°–153°, which was used without further purification.

A solution of 2,2'-(5-hydroxymethyl-1,3-phenylene)di-(2-methylpropiononitrile), (3.8 g) and pyridine (1.58 g) in dichloromethane (10 ml) was stirred, and cooled in an ice bath, while thionyl chloride (3 g) was added over 10 minutes. The solution was kept at room temperature for 2 h and then heated under reflux for 1 h and evaporated to dryness under reduced pressure The residue was partitioned between water and ethyl acetate and the organic phase was separated, dried and evaporated to dryness under reduced pressure to give 2,2'-(5-chloromethyl-1,3-phenylene)di(2-methylpropiononitrile), which was used without further purification.

EXAMPLES 9–16

The process described in Example 8 was repeated, using the appropriate chloromethyl or bromomethyl derivative and the appropriate heterocyclic starting materials, to give the following compounds:

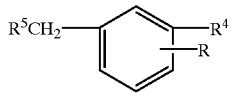

| Ex | $R^5$ | $R^4$ | R | Position of R | Mp | Foot-Notes |
|---|---|---|---|---|---|---|
| 9 | 1H-1-I* | $—C(CH_3)_2CN$ | $—C(CH_3)_2CN$ | 3 | 125–127 | 1 |
| 10 | 1H-I | H | $—C(CH_3)_2CN$ | 3 | 62–65 | |
| 11 | 1H-1-T* | H | $—C(CH_3)_2CN$ | 3 | | 2 |
| 12 | 4H-4-T | H | $—C(CH_3)_2CN$ | 3 | | 3 |
| 13 | 1H-1-I | H | $—C(CH_3)_2CN$ | 4 | 65–66 | |
| 14 | 1H-1-T | H | $—C(CH_3)_2CN$ | 4 | | 4 |
| 15 | 1H-1-I | H | $—CH_2CN$ | 3 | 146–147 | 5 |
| 16 | 1H-1-I | $COOCH_3$ | $—C(CH_3)_2CN$ | 3 | 69–70 | |

*I = imidozyl;
T = 1,2,4-triazolyl
Footnotes
1. Crystallized from toluene/petroleum ether, (bp 60–80°).
2. Nmr in deuteriochloroform; δ 8.12(1H, s), 7.98(1H, s), 7.35–7.6(3H, m), 7.2(1H, m), 5.39(2H, s), 1.72(6H, s).
3. Nmr in deuteriochloroform; δ 8.2(2H, s), 7.25–7.55(3H, m), 7.1(1H, m), 5.2(2H, s), 1.7(6H, s).
4. Nmr in deuteriochloroform; δ 8.12(1H, s), 8.0(1H, s), 7.5(2H, d), 7.3(2H, d), 5.4(2H, s), 1.72(6H, s).
5. Hydrochloride salt.

The compound of Example 9 was prepared from the chloromethyl starting material described in Example 8; and the compounds of Examples 10–16 were prepared from the corresponding bromomethyl starting materials, made by the sequence of reactions described in the second part of Example 1, and used without further purification.

EXAMPLE 17

The process described in Example 8 was repeated, using imidazole in place of 1,2,4-triazole, and 2,2'-[5-(1-chloroethyl)-1,3-phenylene]di(2-methylpropiononitrile), (obtained as described in the second part of Example 7), as the starting materials, to give 2,2'-[5-(1-[imidazol-1-yl] ethyl)-1,3-phenylene]di(2-methylpropiononitrile), mp. 77°–80°.

EXAMPLE 18

A solution of 2-methyl-2-[3-(imidazol-1-ylmethyl) phenyl]-propiononitrile, obtained as described in Example 10, (0.2 g) in concentrated sulphuric acid (0.5 ml) was kept at room temperature for 18 h, diluted to 5 ml with ice water, neutralised with concentrated aqueous ammonia, and extracted three times with ethyl acetate. The extracts were combined, dried and evaporated to dryness under reduced pressure, and the residue was purified by flash column chromatography, eluting with methanol:chloroform (2:23 by volume), to give 2-methyl-2-[3-(imidazol-1-ylmethyl) phenyl]propionamide, mp. 79°–82°.

EXAMPLES 19–20

The process described in Example 18 was repeated, using as starting material the product of Example 1, to give 2-[3-(1-cyano-1-methylethyl)-5-(1H-1,2,4-triazol-1-ylmethyl)phenyl]-2-methylpropionamide, (eluted from the flash chromatography column with methanol:ethylacetate, 1:3 by volume), mp. 134 135°; and 2,2'-[5-(1H-1,2,4-triazol-1-ylmethyl)-1,3-phenylene]di(2-methylpropionamide), mp. 51°–53°, eluted from the flash chromatography column with methanol:ethyl acetate, (1:2 by volume).

EXAMPLE 21

The product from Example 16 (0.12 g) and concentrated aqueous ammonia (3 ml) were stirred together at room temperature for 72 h. The insoluble product was filtered off, washed with water and dried to give 3-(1-cyano-1-methylethyl)-5-(imidazol-1-ylmethyl)benzamide, mp. 149°–150°.

EXAMPLE 22

The process described in Example 21 was repeated, using the product of Example 4 as the starting material, to give 3-(1-cyano-1-methylethyl)-5-(1H-1,2,4-triazol-1-ylmethyl) benzamide, mp. 144°–145°.

EXAMPLE 23

A mixture of the product from Example 22 (0.41 g), pyridine (0.25 ml) and 1,4-dioxan (5 ml) was stirred while trifluoroacetic anhydride (0.24 ml) was added dropwise The resulting solution was kept at room temperature for 18 h, diluted with water (10 ml), made basic with sodium hydrogen carbonate and extracted three times with ethyl acetate. The extracts were combined, dried and evaporated to dryness, and the residue was purified by flash column chromatography, eluting with methanol:chloroform (3:97 by volume) to give 3-(1-cyano-1-methylethyl)-5-(1H-1,2,4-triazol-1-ylmethyl)benzonitrile, mp. 90°–92°.

EXAMPLE 24

The process gdescribed in Example 23 was repeated, using the product of Example 21 as the starting material, to give 3-(1-cyano-1-methylethyl)-5-(imidazol-1-ylmethyl) benzonitrile, mp. 89°–92°.

EXAMPLE 25

The process described in Example 22 was repeated, using piperidine in place of aqueous ammonia, and heating at 80° for 72 h to give 2-methyl-2-[3-piperidinocarbonyl-5-(1H-1,2,4-triazol-1-ylmethyl]propiononitrile. Nmr in deuteriochloroform, δ 8.2(1H,s), 8.0(1H,s), 7.48(1H,m), 7.44(1H,m), 7.2(1H,m), 5.4(2H,s), 3.68(2H,m), 3.27(2H,m), 1.4 1.8(12H,m).

EXAMPLE 26

The process described in Example 25 was repeated, using morpholine in place of piperidine, to give 2-methyl-2-[3-morpholinocarbonyl-5-(1H-1,2,4-triazol-1-ylmethyl]-propiononitrile. Nmr in deuteriochloroform, δ 8.18(1H,s), 8.0(1H,s), 7.5(1H,m), 7.45(1H,m), 7.2(1H,m), 5.4(2H,s), 3.5–3.9(8H,m), 1.72(6H,s).

EXAMPLE 27

A mixture of the product of Example 4 (1.5 g), lithium borohydride (0.23 g) and tetrahydrofuran (5 ml) was heated under reflux for 1 h, then cooled and stirred while 2N aqueous hydrochloric acid was added dropwise until the solution remained acidic, then stirred at room temperature for 1 h and basified by the addition of sodium hydrogen carbonate. The mixture was extracted three times with ethyl acetate, the combined extracts were dried and evaporated to dryness under reduced pressure, and the residue was purified by flash column chromatography, eluting with methanol:chloroform (1:24 by volume), to give 2-[3-hydroxymethyl-5-(1H-1,2,4-triazol-1-ylmethyl)phenyl]-2-methylpropiononitrile, mp. 111°–113°.

EXAMPLE 28

A solution of the product from Example 27 (1 g) and thionyl chloride (0.4 ml) in dichloromethane (5 ml) was heated under reflux for 0.5 h, then evaporated to dryness under reduced pressure, to give 2-[3-chloromethyl-5-(1H-1,2,4-triazol-1-ylmethyl)phenyl]-2-methylpropiononitrile hydrochloride, mp. 189°–190° after trituration with ethyl acetate.

EXAMPLE 29

A mixture of the product from Example 28 (0.73 g), tetrabutylammonium bromide (0.01 g), potassium cyanide (0.52 g), dichloromethane (2 ml) and water (2 ml) was heated under reflux for 3 h. It was then cooled, water (20 ml) was added, and the mixture was extracted three times with ethyl acetate. The extracts were combined, dried and evaporated to dryness under reduced pressure, and the residue was purified by flash column chromatography, eluting with methanol:ethyl acetate (3:97 by volume), to give 3-(1-cyano-1-methylethyl)-5-(1H-1,2,4-triazol-1-ylmethyl)phenylacetonitrile. Nmr in deuteriochloroform: δ 8.18(1H,s), 8.0(1H,s), 7.42(1H,m), 7.38 (1H,m), 7.18(1H,m), 5.4(2H,s), 3.78(2H,s), 1.72(6H,s).

EXAMPLE 30

A mixture of the product from Example 28 (0.6 g), S-methylthiouronium sulphate (0.56 g), 10N aqueous sodium hydroxide (1 ml) and dimethylformamide (5 ml) was stirred at room temperature for 18 h, diluted with water (20 ml) and extracted twice with dichloromethane. The extracts were combined, dried and evaporated to dryness under reduced pressure, and the residue was purified by flash column chromatography, eluting with methanol:ethyl acetate (1:49 by volume) to give 2-methyl-2-[3-methylthiomethyl-5-(1H-1,2,4-triazol-1-ylmethyl)phenyl]-propiononitrile. Nmr in deuteriochloroform: δ 8.12(1H,s), 8.0(1H,s), 7.4(1H,m), 7.27(1H,m), 7.15(1H,m), 5.38(2H,s), 3.66(2H,s), 2.0(3H,s), 1.72(6H,s).

EXAMPLE 31

A solution of the product of Example 30 (0.16 g) in methanol (0.5 ml) and tetrahydrofuran (5 ml) was stirred while a solution of sodium periodate (0.15 g) in water (0.5 ml) was added, and was then stirred at room temperature for a further 18 h. Water (5 ml) was added and the mixture was extracted six times with dichloromethane. The extracts were combined, dried and evaporated to dryness, and the residue was purified by flash column chromatography, eluting with methanol:ethyl acetate (1:9 by volume) to give 2-methyl-2-[3-methylsulphinylmethyl-5-(1 H-1,2,4-triazol-1-ylmethyl)phenyl]-propiononitrile. Nmr in deuteriochloroform; δ 8.16(1H,s), 8.0(1H,s), 7.38(1H,m), 7.27(1H,m), 7.15(1H,m), 5.4(2H,s), 3.98(1H,d), 3.88(1H,d), 2.5(3H,s), 1.72(6H,s).

EXAMPLE 32

A solution of the product of Example 5 (0.25 g) in tetrahydrofuran (5 ml) was cooled to 0° and stirred under an atmosphere of argon while a solution of methylmagnesium chloride in tetrahydrofuran (3M, 0.5 ml) was added over 5 minutes. The solution was stirred for a further 0.5 h, then treated with saturated aqueous ammonium chloride solution and extracted twice with ethyl acetate. The extracts were combined, dried and evaporated to dryness under reduced pressure, and the residue was purified by flash column chromatography, e luting with methanol:ethyl acetate (1:19 by volume) to give 2-[3-(1-hydroxy-1-methylethyl)-5-(5-methylimidazol-1-ylmethyl)phenyl]-2-methylpropiononitrile, mp. 128°–131° after trituration with pentane.

EXAMPLE 33

The process described in Example 32 was repeated, using the product from Example 4 as the starting material, to give 2-[3-(1-hydroxy-1-methylethyl)-5-(1 H-1,2,4-triazol-1-ylmethyl)phenyl]-2-methylpropiononitrile, mp. 152°–154°, after crystallisation from diethyl ether.

EXAMPLE 34

A solution of 3-bromopyridine (0.31 g) in diethyl ether was stirred and cooled to −70° while a solution of n-butyllithium in hexane (1.6M, 1.33 ml) was added, followed by 2,2'-(5 formyl-1,3-phenylene)di(2-methylpropiononitrile), (0.48 g). The mixture was allowed to warm to room temperature and was then extracted with 2N aqueous hydrochloric acid (10 ml). The acid extract was separated, basified with 10N aqueous sodium hydroxide solution and extracted twice with ethyl acetate. The extracts were combined, dried and evaporated to dryness under reduced pressure, and the residue was purified by flash column chromatography, eluting with ethyl acetate, to give 2,2'-[5-(1-hydroxy-1-(3-pyridyl]methyl)-1,3-phenylene]di(2-methyl propiononitrile), mp. 117°–120°.

EXAMPLE 35

A solution of the product from Example 34 (50 mg) in dichloromethane (2 ml) and thionyl chloride (0.1 ml) was heated under reflux for 1 h, then evaporated to dryness under reduced pressure. The residue was dissolved in ethanol, 10% palladium-on-carbon catalyst was added, and the mixture was shaken in an atomosphere of hydrogen at room temperature and atmospheric pressure for 1 h. The mixture was filtered, the filtrate was evaporated to dryness under reduced pressure, and the residue was partitioned between aqueous sodium hydrogen carbonate solution and ethyl acetate. The ethyl acetate phase was separated, dried and evaporated to dryness under reduced pressure, and the residue was purified by flash column chromatography, eluting with ethyl acetate, to give 2,2'-[5-(3-pyridylmethyl)-1,3-phenylene]di(2-methylpropiononitrile), mp 82°–84°.

EXAMPLE 36

A mixture of 2,2'-(5 formyl-1,3-phenylene)di(2-methylpropiononitrile (0.48 g), trimethylsulphoxonium iodide (0.53 g), powdered potassium hydroxide (0.27 g), 1 H-1,2,4-triazole (0.16 g) and tert-butyl alcohol (5 ml) was stirred at 80° for 1 h, then cooled, diluted with water (10 ml) and extracted three times with ethyl acetate. The combined extracts were dried and evaporated to dryness under reduced pressure, and the residue was purified by flash column chromatography, eluting with methanol:ethyl acetate (1:49 by volume) to give 2,2'-[5-(1-hydroxy-2-(1H-1,2,4-triazol-1-yl]ethyl)-1,3-phenylene]di(2-methylpropiononitrile, mp 131°–134°.

EXAMPLE 37

A mixture of 2,2'-[5-(E-2-[1H-1,2,4-triazol-1-yl]vinyl)-1,3-phenylene]di(2-methylpropiononitrile), (25 mg), 10% palladium-on-carbon catalyst (10 mg) and ethyl acetate (2 ml) was stirred in an atmosphere of hydrogen at room temperature and atmospheric pressure for 1 h. The mixture was filtered, and the filtrate was evaporated to dryness under reduced pressure to give 2,2'-[5-(2H-1,2,4-triazol-1-yl-methyl]ethyl)-1,3-phenylene]di(2-methylpropiononitrile), mp 102°–104°.

The required starting material for use in the above process may be manufactured as follows:

A solution of the product from Example 36 (0.25 g), thionyl chloride (0.2 ml) and dichloromethane (2 ml) was heated under reflux for 1 h, then evaporated to dryness. The residue was triturated with ethyl acetate to give 2,2'-[5-(1-chloro-2[1H-1,2,4-triazol-1-yl]ethyl)-1,3-phenylene]di(2-methyl-propiononitrile) hydrochloride, mp 190°–192°.

A mixture of this material (70 mg), sodium 1 H-1,2,4-triazole (100 mg) and dimethylformamide (1 ml) was heated at 90° for 2 h, then diluted with water (10 ml) and extracted with ethyl acetate. The extract was dried and evaporated to dryness under reduced pressure, and the residue was purified by flash column chromatography, eluting with ethyl acetate:n-pentane (3:1 by volume) to give the required starting material, mp 108°–109°.

EXAMPLE 38

A solution of oxalyl chloride (0.12 ml) in dichloromethane (2 ml) was stirred and cooled to 70° while dimethyl sulphoxide (0.12 ml) was added dropwise. The solution was stirred for 2 minutes, then 2-[3-(1-hydroxyethyl)-5-(1 H-1,2,4-triazol-1-ylmethyl)phenyl]-2-methylpropiononitrile, (0.18 g), was added, and the temperature was kept at −70° for 10 minutes. Triethylamine (0.2 ml) was added, and the mixture was allowed to warm to room temperature. Water (15 ml) was added, and the mixture was extracted three times with dichloromethane. The extracts were combined, dried and evaporated to dryness, and the residue was purified by flash column chromatography, eluting with methanol:chloroform (1:99 by volume) to give 2-[3 acetyl-5-(1 H-1,2,4-triazol-1 ylmethyl)phenyl]-2-methylpropiononitrile. Nmr in deuteriochloroform; δ 8.2 (1H,s), 8.02(2H,m), 7.8(1H,m), 7.64(1H,m), 5.45(2H,s), 2.6 (3H,s), 1.75(6H,s).

The 1-hydroxyethyl starting material used in the above process may be manufactured as follows:

The product from Example 27 was oxidised by the process described in the first part of this Example to the corresponding 3-formyl compound.

The formyl compound (0.2 g) was dissolved in tetrahydrofuran ml), stirred and cooled to 70° under an atmosphere of argon, and a solution of methylmagnesium chloride in tetrahydrofuran (3 m, 0.32 ml) was added. The mixture was stirred at 70° for 0.5 h and allowed to warm to room temperature, then saturated aqueous ammonium chloride solution (10 ml) was added. The mixture was extracted three times with dichloromethane, and the extracts were combined, dried and evaporated to dryness under reduced pressure to give the required 1-hydroxyethyl starting material, which was used without further purification.

EXAMPLES 39–48

The process described in Example 1 was repeated, using the appropriate 5-methyl-1,3-disubstituted phenylene compound as starting material, to give the following compounds:

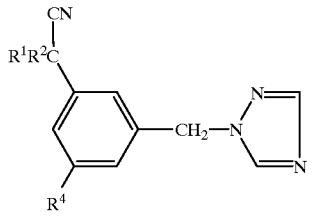

| Ex. | $R^1 = R^2$ | $R^4$ | Mp. | Footnotes |
|---|---|---|---|---|
| 39 | $CH_3$ | $CH_3$ | 79–81 | 1 |
| 40 | $CH_3$ | $—C(CH_3)(C_2H_5),CN$ | — | 2,3 |
| 41 | $CH_3$ | $—C(C_2H_5)_2,CN$ | — | 4,5 |
| 42 | $CH_3$ | 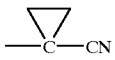 | 45–48 | 6 |
| 43 | $CH_3$ | 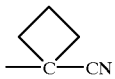 | 68–69 | 7 |

-continued

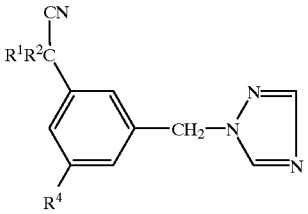

| Ex. | $R^1 = R^2$ | $R^4$ | Mp. | Footnotes |
|---|---|---|---|---|
| 44 | $CH_3$ | 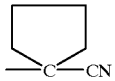 | — | 8,9 |
| 45 | $CD_3$ | $—C(CD_3)_2,CN$ | 82–83 | 10 |
| 46 | $CH_3$ | $—C(CH_2F)_2, CN$ | — | 11,12 |
| 47 | $CH_3$ | —Br | 156–158 | 13,14 |
| 48 | $CH_3$ | $—C(CH_3)_2,SO_2CH_3$ | 105–107 | 15 |

Footnotes

1. The required starting material was prepared as follows:
A mixture of 3,5-dimethylbenzyl bromide (25 g), tetrabutylammonium bromide (1.2 g), potassium cyanide (12.3 g), dichloromethane (25 ml) and water (20 ml) was stirred vigorously and heated under reflux for 2 h. The mixture was cooled and diluted with dichloromethane, and the organic phase was separated, dried and evaporated to dryness under released pressure. The residue was purified by flash column chromatography, eluting with petroleum ether (bp 60–80°):ethyl acetate (19:1 by volume), to give 3,5-dimethylphenylacetonitrile, m.p. 42–44°.
A mixture of this nitrile (12.5 g) and sodium hydride (80% dispersion in mineral oil, 6.45 g) was cooled in ice and stirred under an atmosphere of argon, while a solution of iodomethane (25 ml) in dimethylformamide (50 ml) was added dropwise over 0.5 h. The mixture was allowed to warm to room temperature, stirred at room temperature for a further 0.5 h, then added cautiously to ice-water (500 ml). The mixture was extracted three times with diethyl ether, and the extracts were combined and evaporated to dryness.
The residue was purified by flash column chromatography, eluting with petroleum ether (bp 60–80°):
ethyl acetate (19:1 by volume), to give the required starting isothiuronium sulphate (1.39 g), dimethylformamide (10 ml) and 10N aqueous sodium hydroxide (2 ml). The mixture was stirred for 1 h, diluted with water and extracted with diethyl ether, the extract was dried and evaporated to dryness under reduced pressure and the residue was purified by flash chromatography, eluting with ethyl acetate (5% by volume) in pentane, to give 2-methyl-2-[3-methyl-5-(methylthiomethyl)phenyl]propiononitrile.
A solution of this nitrile (0.63 g) in dichloromethane (20 ml) was treated with m-chloroperbenzoic acid (1.2 g), added in portions over 10 minutes, then the mixture was stirred for 0.5 h. The mixture was then washed twice with 2N aqueous sodium hydroxide, dried and evaporated to dryness, to give 2-methyl-2-[3-methyl-5-(methylsulphoylmethyl)phenyl]propionitrile, which was used without purification.
A mixture of this nitrile (0.25 g), iodomethane (0.35 g), sodium hydride (80% dispersion in oil, 0.12 g) and dimethylformamide (5 ml) was stirred under an atmosphere of argon at room temperature for 18 hr. The mixture was treated with water and extracted twice with ethyl acetate, and the extracts were combined and evaporated to dryness. The residue was then triturated with tetrachloromethane to give 2-methyl-2-[3-methyl-5-(1-methylsulphonyl-1-methylethyl)-phenyl]propionitrile, m.p. 129–131°.

EXAMPLES 49–52

The process described in Example, 1 was repeated, using the appropriate 2- or 4-substituted 2,2-(5-methyl-1,3-phenylene)di(2-methylpropiononitrile) as starting material, to give the following compounds:

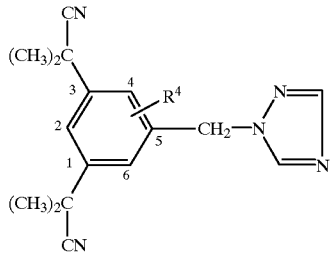

| Ex | $R^4$ | Position of substitution | Mp. | Footnote |
|---|---|---|---|---|
| 49 | $NO_2$ | 4 | — | 1,2 |
| 50 | Br | 4 | 83–86 | 3 |
| 51 | Br | 2 | 128–131 | 3 |
| 52 | CN | 4 | 35–37 | 4 |

Footnotes

1. Nmr in deuteriochloroform; δ 8.18(1H, s), 8.0(1H, s), 7.82(1H, d), 7.46(1H, d), 5.34(2H, s), 1.86(6H, s), 1.72(6H, s), 2. The required starting material was prepared as follows: 2,2'-(5-methyl-1,3-phenylene)di(2-methylpropiononitrile), (0.23 g) was added to a 0.5M solution of nitronium tetrafluoroborate in sulphate (2 ml), and the mixture was stirred at 55° for 24 h. The cooled mixture was treated with water and extracted with ether. The ether extract was dried and evaporated to dryness under reduced pressure, and the residue was purified by flash chromatography using ethylacetate (15% by volume) in petroleum ether as eluant to give 2,2'-(5-methyl-4-nitro-1,3-phenylene)di(2-methylpropionitrile) mp 82–85°.

3. The required starting material was prepared as follows:- A mixture of 2,2'-(5-methyl-1,3-phenylene)di(2-methyl-propiononitriie), (1.13 g), dichloromethane (10 ml) and silver tri-fluoromethanesulphonate (1.55 g) was stirred in the dark while adding a solution of bromine (0.88 g) in dichloromethane (2 ml) dropwise over 5 minutes. The mixture was stirred for a further 1 h, then treated with dilute aqueous potassium bicarbonate and ethyl acetate. The mixture was filtered through a pad of kieselguhr ("Celite"-trade mark), and the organic phase was separated, dried and evaporated to dryness. The residue was subjected to flash chromatography eluting with ethyl acetate (15% by volume in pentane to give 2,2'-(4-bromo-5-methyl-1,3-phenylene)di(2-methylpropiononitrile) mp 121–122°. Further elution with ethyl acetate (25% by volume) in pentane gave 2,2'-(2-bromo-5-methyl-1,3-phenylene)di(2-methyl-propiononitrile) mp 141–149°.

4. The required starting material was prepared as follows:- A mixture of 2,2'-(4-bromo-5-methyl-1,3-phenylene)di(2-methylpropionitrile), (0.2 g), cuprous cyanide (0.09 g) and di-methylformide (0.5 ml) was stirred under reflux for 4 h. A further 0.09 g of cuprous cyanide was added, and the mixture was heated for a further 18 h. The mixture was cooled, treated with warm aqueous sodium cyanide solution and extracted with ethyl acetate. The extract was dried and evaporated to dryness under reduced pressure, and the residue was purified by flash chromatography, eluting with ethyl acetate (20% by volume) in petroleum ether (pb 60–80°) to give 2,2'-(4-cyano-5-methyl-1,3-phenylene)di(2-methylpropiono-nitrile) mp 84–86°.

EXAMPLE 53

A mixture of 2,2'-(5-chlorodideuteriomethyl-1,3-phenylene)-di(2-trideuteriomethyl-3,3,3-trideuteriopropiononitrile) (0.65 g), dimethylformamide (5 ml) and sodium triazole (0.45 g) was stirred at room temperature for 18 h. The mixture was diluted with water (30 ml) and extracted with ethyl acetate, and the extract was dried and evaporated to dryness under reduced pressure. The residue was purified by flash chromatography, using ethyl acetate as eluant, to give 2,2'-[5-dideuterio-(1H-1,2,4-triazol-1-yl)methyl-1,3-phenylene]-di(2-trideuteriomethyl-3,3,3-trideuteriopropiononitrile), mp 82°–83° after crystal-lisation from ethyl acetate/cyclohexane.

The starting material from the above process may be prepared as follows:

The process used to prepare methyl 3,5-bis(1-cyano-1-methylethyl)benzoate, described in the later part of Example 8, was repeated, using trideuterioiodomethane instead of iodomethane, to give methyl 3,5-bis[1-cyano-2,2,2-trideuterio-1-(trideuteriomethyl)ethyl]-benzoate, m.p. 83°–84°.

A solution of this methyl ester (7.7 g) in tetrahydrofuran (100 ml) was stirred at −50° under an atmosphere of argon, while lithium aluminium deuteride (0.63 g) was added in portions over 10 minutes at −40° to −50°. The solution was then allowed to warm to room temperature, and kept at room temperature for 0.5 h. The solution was then treated with ethyl acetate (5 ml), cautiously acidified with 2N aqueous hydrochloric acid, and filtered through a pad of kieselguhr ("Celite"), washing the pad with ethyl acetate (2×50 ml). The organic phase was separated, dried and evaporated to dryness under reduced pressure, to give 2,2'-[5-dideuterio (hydroxy)methyl)-1,3-phenylene]di[3,3,3-trideuterio-2-(dideuteriomethyl)propiononitrile], mp 152°–154°.

An ice-cooled solution of this compound (6.8 g) in dichloromethane (30 ml) and thionyl chloride (3 ml) was stirred while pyridine (2.35 g) was added dropwise over 15 minutes. The mixture was stirred at room temperature for a further 2 h, and then evaporated to dryness under reduced pressure. The residue was partitioned between ethyl acetate and water, and the ethyl acetate phase was separated, dried and evaporated to dryness under reduced pressure, to give 2,2'-[5-(chlorodideuteriomethyl)-1,3-phenylene]di[3,3,3-trideuterio-2-(trideuteriomethyl)propiononitrile] mp 119°–121°.

EXAMPLES 54–57

The process described in Example 53 was repeated, using the appropriate chloromethyl or chlorodideuteriomethyl starting material, to give the following compounds:

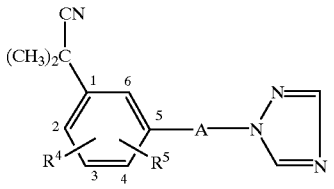

| Ex | $R^4$ | Position of substitution | $R^5$ | Position of substitution | A | Mp | Footnote |
|---|---|---|---|---|---|---|---|
| 54 | — | — | —$C(CH_3)_2CN$ | 3 | $CD_2$ | 82–83 | 1 |
| 55 | — | — | —$C(CH_3)_2CN$ | 4 | $CH_2$ | 95–98 | 2 |
| 56 | —Br | 2 | — | — | $CH_2$ | — | 3,4 |
| 57 | —F | 2 | —$C(CH_3)_2CN$ | 3 | $CH_2$ | — | 5,6 |

Footnotes

1. Starting material was prepared from 2,2'-(5-methyl-1,3-phenylene)di(2-methylpropiononitrile) by reduction with lithium aluminium deuteride followed by chlorination with thionyl chloride, as described in the latter part of Example 53, to give 2,2'-(5-chlorodideuteriomethyl-1,3-phenylene)di(2-methylpropiononitrile), mp 119–121°.
2. the starting material was prepared by the process described in the latter part of Example 8, using methyl 2,5-dimethylbenzoate in place of methyl 3,5-dimethylbenzoate.
3. Nmr is deuteriochloroform: δ8.14(1H, s), 7.98(1H, s), 7.65(1H, d), 7.48(1H, d), 7.06(1H, dd), 5.35(2H, s), 1.86(6H, s).
4. The starting material was prepared by the process described in the latter part of Example 8, using methyl 4-bromo-3-methylbenzoate in place of methyl 3,5-dimethylbenzoate.
5. Nmr is deuteriochloroform: δ8.18(1H, s), 8.0(1H, s), 7.44(2H, d), 5.36(2H, s), 1.8(6H, s).
6. The starting material was prepared as follows:- 2-Fluoro-m-xylene (5 g) was added dropwise to a stirred solution of aluminium chloride (6.4 g) and acetyl chloride (2.7 ml) in dichloroethane (20 ml), and the mixture was stirred at room temperature for 1.5 h. The mixture was treated with cold 1N aqueous hydrochloric acid (100 ml), the organic layer was separated and the aqueous phase was further extracted with dichloromethane. The combined extracts were dried and evaporated to dryness under reduced pressure, and the residue was purified by flash chromatography using ethyl acetate (10% by volume) in petroleum ether (bp 60–80°) as eluant, to give 4-fluoro-3,5-dimethylacetophenone.
A mixture of this acetophenone (4 g), methanol (40 ml) and sodium hypochlorite solution (60 ml) was stirred at reflux for 0.5 h. The cooled reaction mixture was diluted to 500 ml with water , and stirred while sodium sulphite (10 g) was added. The solution was washed with ethyl acetate, and the aqueous phase was acidified with concentrated hydrochloric acid and then extracted three times with ethyl acetate. The combined extracts were dried and evaporated to dryness to give 4-fluoro-3,5-dimethylbenzoic acid, mp 165–167°.
A mixture of the acid (6.7 g), methanol (100 ml) and concentrated sulphuric acid (4 ml) was heated under reflux for 2 h. The methanol was evaported under reduced pressure, and the residue was washed with water (200 ml), then extracted twice with ethyl acetate. The combined ethyl acetate extracts were washed with 2N-aqueous sodium hydroxide, dried and evaporated to dryness under reduced pressure, to give methyl 4-fluoro-3,5-dimethylbenzoate which was used without further purification.
The methyl 4-fluoro-3,5-dimethylbenzoate was used in place of methyl 3,5-dimethylbenzoate in the processes described in the latter part of Example 8, to give 2,2'-(5-chloromethyl-2-fluoro-1,3-phenylene)di(2-methylpropiononitrile), mp 118–120°.

EXAMPLE 58

A mixture of 2,2'-[5-(5-formylimidazol-1-yl)-1,3-phenylene]-di(2-methylpropiononitrile), (0.17 g), ethanol (3 ml), sodium acetate (0.21 g), hydroxylamine hydrochloride (0.17 g), and water (2 ml) was heated under reflux for 1 h. The mixture was diluted with water (10 ml) and extracted twice with ethyl acetate, and the combined extracts were dried and evaporated to dryness under reduced pressure.

A solution of the residue and pyridine (0.08 ml) in dioxan (2 ml) was stirred and cooled in an ice bath while trifluoroacetic anhydride (0.08 ml) was added, and the mixture was kept at room temperature for 18 h. The mixture was treated with saturated sodium hydrogen carbonate solution (10 ml) and extracted three times with dichloromethane, and the combined extracts were dried and evaporated to dryness under reduced pressure. The residue was purified by flash chromatography using methanol (2% by volume) in chloroform as eluant, to give 2,2'-[5-(5-cyanoimidazol-1-yl)-1,3-phenylene]di(2-methylpropiononitrile), mp 88°–90°.

The starting material for the above process was obtained as follows:

A suspension of ethyl imidazole-4-carboxylate (1.4 g), triethylamine (1.2 g) and chloroform (20 ml) was stirred at room temperature while trityl chloride (3.06 g) was added, and the mixture was stirred at room temperature for 1 h. The resulting solution was washed with water, dried and evaporated to dryness under reduced pressure, and the residue was crystallised from a mixture of ethyl acetate and cyclohexane, to give ethyl 1-tritylimidazole-4-carboxylate, mp 163°–164°.

A solution of this ethyl ester (1 g) in dichloromethane (10 ml) under an atmosphere of argon at 70° was stirred while a 1M solution of di-isobutylaluminium hydride in dichloromethane (5.3 ml) was added dropwise, and the mixture was then stirred at −70° for a further 0.5 h. Ethyl acetate (1 ml) was added dropwise, followed by a saturated aqueous solution of ammonium chloride (15 ml), the mixture was filtered and the filtrate was diluted with ethyl acetate. The organic phase was separated, dried and then evaporated to dryness to give 4-formyl-1-tritylimidazole, mp 176°–179°.

A mixture of 4-formyl-1-tritylimidazole (0.5 g), 2,2'-(5-bromomethyl-1,3-phenylene)di(2-methylpropiononitrile)

and acetonitrile (2 ml) was heated under reflux for 30 h. The reaction mixture was treated with acetic acid (8 ml) and water (2 ml) and the mixture was then heated at 90° for 1 h. The mixture was diluted with water (20 ml) and washed with ether, the aqueous phase was basified with sodium carbonate, and the mixture was extracted three times with ethyl acetate. The combined extracts were dried and evaporated to dryness, and the residue was purified by flash chromatography using methanol (2% by volume) in chloroform as eluant, to give 2,2'-[5-(5-formylimidazol-1-yl)-1,3-phenylene]di(2-methylpropiononitrile), mp 108°–111°.

EXAMPLE 59

A solution of 1,2,4-triazole (0.69 g) in trifluoroacetic acid (3.12 ml) was added to 2,2'-[5-(1-hydroxy-1-methylethyl)-1,3-phenylene]-di(2-methylpropiononitrile), (0.27 g), and the resulting solution was stirred at room temperature for 18 hr and then evaporated to dryness. The residue was treated with aqueous sodium hydrogen carbonate solution and the mixture was extracted with ethyl acetate. The extract was dried and evaporated to dryness under reduced pressure, and the residue was purified by flash chromatography using methanol (1% by volume) in dichloromethane as eluant, to give 2,2'-(5-[1-methyl-1-(1H-1,2,4-triazol-1-yl)ethyl]-1,3-phenylene)di(2-methylpropiononitrile), which was characterised as the hydrochloride salt, mp 185°–188°.

The starting material for the above example may be prepared as follows:

A 3M solution of methylmagnesium chloride in tetrahydrofuran (3 ml) was added over 5 minutes to a stirred solution of methyl 3,5-bis-(1-cyano-1-methylethyl)benzoate (1.35 g) in tetrahydrofuran (20 ml) at −60° under an atmosphere of argon. The mixture was allowed to warm to room temperature and kept at room temperature for 0.5 h, then treated with 1N aqueous hydrochloric acid solution (20 ml). The mixture was extracted twice with ethyl acetate and the combined extracts were dried and evaporated to dryness under reduced pressure, to give 2,2'-[5-(1-hydroxy-1-methylethyl)-1,3-phenylene]di(2-methylpropiononitrile) which was used without further purification.

EXAMPLE 60

The process described in Example 34 was repeated, using 5-bromopyrimidine instead of 3-bromopyridine, and a reaction temperature of −110°, to give 2,2'-[5-hydroxy(5-pyrimidinyl)methyl]-1,3-phenylene]di(2-methylpropiononitrile), mp 129°–130°.

EXAMPLE 61

A solution of 2,2'-[5-(1-hydroxy-1-(3-pyridyl)methyl)-1,3-phenylene]di(2-methylpropiononitrile) in dichloromethane (2 ml) was stirred under an atmosphere of argon at 70° while diethylaminosulphurtrifluoride (0.07 ml) was added over 5 minutes. The solution was allowed to warm to room temperature over 0.5 h, then treated with aqueous sodium hydrogen carbonate solution, and the mixture was extracted twice with ethyl acetate. The combined extracts were dried and evaporated to dryness under reduced pressure, and the residue was purified by flash chromatography using 2:1 (by volume) ethyl acetate: pentane as eluant to give 2,2'-[5 fluoro(3-pyridyl)methyl-1,3-phenylene]di(2-methylpropiononitrile). Nmr in deuteriochloroform: δ 8.65 (2H, m), 7.7 (1H, d), 7.56 (1H, m), 7.42 (2H, m), 7.38 (1H, m), 6.56 (1H, d), 1.75 (12H, s).

EXAMPLE 62

The process described in Example 61 was repeated, using 2,2'-[5-(1-hydroxy-1-(5-pyrimidinyl)methyl)-1,3-phenylene]di(2-methylpropiononitrile as starting material, to give 2,2'-[5-fluoro(5-pyrimidinyl)methyl-1,3-phenylene]di(2-methylpropiononitrile, mp 72°–74°.

EXAMPLE 63

A solution of 2,2'-[5-nicotinoyl-1,3-phenylene)di(2-methylpropiononitrile) (80 mg) in dichloromethane (1 ml), at 70° under an atmosphere of argon, was treated with diethylaminosulphurtrifluoride (0.3 ml) and the mixture was kept at room temperature for 3 days. The mixture was treated with aqueous sodium hydrogen carbonate solution and extracted twice with diethyl ether. The ether extracts were dried and evaporated to dryness under reduced pressure, and the residue was purified by flash chromatography, using ethyl acetate (40% by volume) in pentane as eluant, to give 2,2'-[5-(1,1-difluoro-1-(3-pyridyl)-methyl)-1,3-phenylene]di(2-methylpropiononitrile). Nmr in $d_6$-dimethylsulphoxide: δ 8.85 (1H, d), 8.75 (1H, d), 8.05 (1H, d), 7.8 (1H, s), 7.68 (2H, s), 7.56 (1H, dd), 1.74 (12H, s).

The nicotinoyl compound used as starting material in the above process was obtained as follows:

A mixture of 2,2'-[5-hydroxy(3-pyridyl)methyl-1,3-phenylene]di(2-methylpropiononitrile) (0.1 g), dichloromethane (3 ml) and pyridinium chlorochromate (0.1 g) was stirred at room temperature for 1 h. The reaction mixture was purified by flash chromatography using ethyl acetate (20% by volume) in dichloromethane as eluant to give 2,2'-[5-nicotinoyl-1,3-phenylene)di(2-methylpropiononitrile), mp 87°–89°.

EXAMPLE 64

Sodium borohydride (20 mg) was added to a solution of 2-[3-(2-oxo-1,1-dimethylpropyl)-5-(1H-1,2,4-triazol-1-ylmethyl)phenyl]-2-methylpropiononitrile (prepared as described in Example 2—40 mg) in ethanol (2 ml) and the mixture was stirred at room temperature for 18 h. The mixture was diluted with water and extracted with ethyl acetate, and the extract was dried and evaporated to dryness under reduced pressure. The residue was purified by flash chromatography, using methanol (1% by volume) in ethyl acetate as eluant, to give 2-[3-(2-hydroxy-1,1-dimethylpropyl)-5-(1H-1,2,4-triazol-1-yl-methyl)phenyl]-2-methylpropiononitrile, mp 83°–84°.

EXAMPLE 65

A solution of 2-[3-(1-hydroxy-1-methylethyl)-5-(1H-1,2,4-triazol-1-ylmethyl)phenyl]-2-methylpropiononitrile (0.06 g) in trifluoroacetic acid (1 ml) was treated with triethylsilane (50 mg) and the solution kept at room temperature for 18 h and then evaporated to dryness under reduced pressure. The residue was treated with aqueous sodium hydrogen carbonate solution and the mixture was extracted twice with ethyl acetate. The combined extracts were dried and evaporated to dryness under reduced pressure, and the residue was purified by flash chromatography, using ethyl acetate as eluant, to give 2-[3-isopropyl-5-(1H-1,2,4-triazol-1-ylmethyl)phenyl]-2-methylpropiononitrile. Nmr in deuteriochloroform: δ 8.1 (1H, s), 8.0 (1H, s), 7.32 (1H, m), 7.18 (1H, m), 7.05 (1H, m), 5.35 (2H, s), 2.92 (1H, m), 1.7 (6H, s), 1.24 (6H, d).

EXAMPLE 66

A mixture of 2-[2-bromo-5-(1H-1,2,4-triazol-1-ylmethyl)-phenyl]-2-methylpropiononitrile (0.15 g), dimethylformamide (2 ml) and cuprous cyanide (0.09 g) was stirred and heated under reflux for 8 h. The cooled mixture was treated with aqueous potassium cyanide solution (10 ml) and the mixture was stirred for 10 minutes, then extracted three times with dichloromethane. The combined extracts were dried and evaporated to dryness under reduced pressure, and the residue was purified by flash chromatography, using methanol (2% by volume) in chloroform as eluant, to give 2-[2-cyano-5-(1H-1,2,4-triazol-yl methyl)phenyl]-2-methylpropiononitrile, characterised as the hydrochloride salt mp 159°–166°.

A mixture of 2,2'-[5-bromocyanomethyl-1,3-phenylene] di(2-methylpropiononitrile) (0.33 g), 1,2,4-triazole (0.34 g) and dimethylformamide (2 ml) was stirred at 50° for 24 h. The mixture was treated with water (20 ml), and extracted with ethyl acetate, and the extract was dried and evaporated to dryness under reduced pressure. The residue was purified by flash chromatography, using methanol (3% by volume) in dichloromethane as eluant, to give 2,2'-[5-cyano(1H-1,2,4-triazol-1-yl)methyl-1,3-phenylene]di(2-methylpropiononitrile), characterised as the hydrochloride salt, mp 148°–151°.

The starting material for the above process was obtained as follows:

A mixture of 2,2'-(5-chloromethyl-1,3-phenylene)di(2-methylpropiononitrile), (3.4 g), tetraethylammonium cyanide (3 g), and dichloromethane (10 ml) was stirred at room temperature for 1 h. The reaction mixture was washed three times with water, dried and evaporated to dryness under reduced pressure, and the residue was recrystallised from ethanol to give 2,2'-[5-cyanomethyl-1,3-phenylene)di(2-methylpropiononitrile), mp 72°–73°.

A mixture of this cyanomethyl compound (1 g), 1,2-dichloroethane (1 ml) and bromine (0.23 ml) was heated under reflux for 12 h. The reaction mixture was dissolved in dichloromethane (40 ml) and the solution was washed with water, dried and evaporated to dryness under reduced pressure. The residue was purified by flash chromatography using ethyl acetate (20% by volume) in petroleum ether (bp 60°–80°) as eluant, to give 2,2'-[5-bromocyanomethyl-1,3-phenylene]di(2-methylpropiononitrile), np 108°–111°.

EXAMPLE 68

The process described in Example 67 was repeated, using imidazole instead of 1,2,4-triazole, to give 2,2'-[5-cyano (imidazol-1-yl)methyl-1,3-phenylene]di(2-methylpropiononitrile), mp 136°–138°.

EXAMPLE 69

A 20% (w/v) solution of sodium nitrite in water was added dropwise in a stirred mixture of 4 amino-1-[3,5-bis (1-cyano-1-methylethyl)benzyl]-1H-1,2,4-triazolium bromide and 2N aqueous hydrochloric acid (10 ml), until a slight excess of nitrite was present. The solution was washed with ether, neutralised with sodium hydrogen carbonate, and extracted twice with ethyl acetate. The combined ethyl acetate extracts were dried and evaporated to dryness and the residue was recrystallised from a mixture of ethyl acetate and cyclohexane to give 2,2'-[5-(1H-1,2,4-triazol-1-yl-methyl)-1,3-phenylene)di(2-methylpropiononitrile, mp 81°–82°.

The starting material for the above example was obtained as follows:

A mixture of 2,2'-(5-bromomethyl-1,3-phenylene)di(2-methylpropiononitrile), (3.05 g), 4 amino-1H-1,2,4-triazole (1.68 g) and acetonitrile (5 ml) was stirred at 50° for 18 h. The mixture was diluted with ethyl acetate (5 ml) and cooled, and the solid which crystallised was filtered off, to give 4 amino-1-[3,5-bis(1-cyano-1-methylethyl)benzyl-1 H-1,2,4-triazolium bromide, mp 195°–197°.

EXAMPLE 70

A mixture of 2,2'-[5-(1-chloro-1-(pyrimidin-5-yl) methyl)-1,3-phenylene]di(2-methylpropi ononitrile), (0.55 g), triethylamine (0.25 ml), 5% palladium-on-carbon (0.02 g) and ethanol (10 ml) was stirred under hydrogen at room temperature and atmospheric pressure for 10 minutes and then filtered. The filtrate was diluted with ethyl acetate (25 ml), and the solution washed with aqueous sodium hydrogen carbonate, dried and evaporated to dryness. The residue was purified by flash chromatography using 1% by volume of methanol in dichloromethane as eluant to give 2,2'-[5-(pyrimidin-5-ylmethyl)-1,3-phenylene]di(2-methylpropiononitrile), mp 132°–134°.

The starting material for the above process was obtained as follows:

A solution of 2,2'-[5-hydroxy-.1-(pyrimidin-5-yl)methyl-1,3-phenylene]di(2-methylpropiononitrile), (0.32 g), in dichloromethane (5 ml) was treated with thionyl chloride (0.11 ml) and the mixture was heated under reflux for 0.5 h. The cooled solution was treated with aqueous sodium hydrogen carbonate solution, and the mixture was stirred for 15 minutes. The organic phase was separated, dried and evaporated to dryness, and the residue was purified by flash chromatography, eluting with 1% by volume of methanol in dichloromethane, to give 2,2'-(5-[1-chloro-1-(pyrimidin-5-yl)methyl]-1,3-phenylene)di(2-methylpropiononitrile), mp 118°–121°.

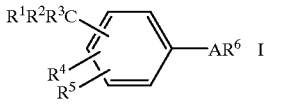

I

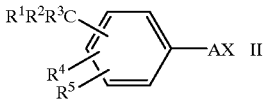

II

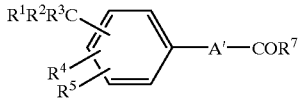

III

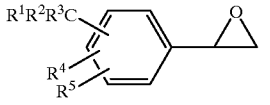

IV

-continued

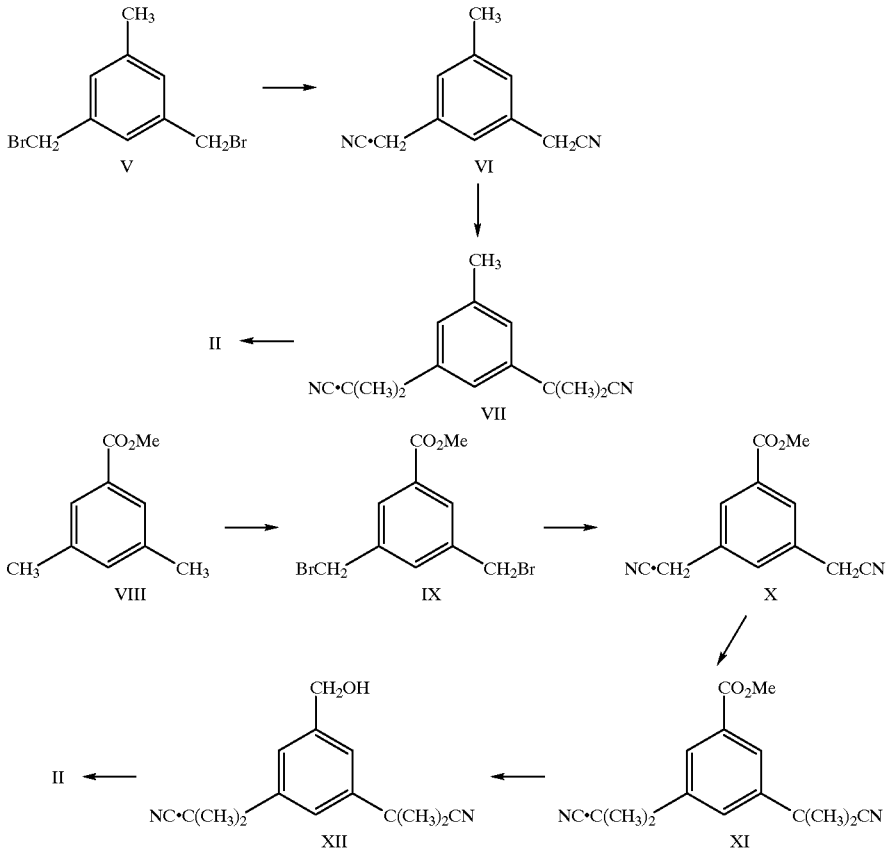

We claim:

[1. A (substituted-aralkyl)heterocyclic compound of the formula I

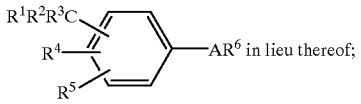

wherein $R^1$ is an azido, carbamoyl, cyano, formyl, hydroxy or nitro radical, a 1–6C 1-hydroxyalkyl, alkoxy, alkylcarbamoyl, alkylthio, alkylsulphinyl or alkylsulphonyl radical, a 2-cyanoethyl radical, optionally bearing one to four 1–6C alkyl substituents, or a 2–6C alkanoyl, halogenoalkanoyl, alkanoyloxy, alkanoylamino, dialkylcarbamoyl or alkoxycarbonyl radical; $R^2$ and $R^3$, which may be the same or different, are each a 1–6C alkyl, deuterioalkyl or halogenoalkyl radical, or $R^1R^2R^3C$-is a 1,1-dicyanoethyl or trifluoromethylsulphonyl radical; $R^4$ is a hydrogen or halogen atom, a cyano or nitro radical or a 1–6C alkyl or halogenoalkyl radical; $R^5$ has any of the values defined above for the group $R^1R^2R^3C$, or has any of the values defined above for $R^4$, or is a carbamoyl, 1-pyrrolidinylcarbonyl, piperidinocarbonyl, morpholinocarbonyl or nitro radical, a 1–6C alkoxy or halogenoalkoxy radical or a 2 6C alkanoyl or alkoxy-carbonyl radical; A is a methylene or ethylene radical optionally bearing one or more substituents selected from the group consisting of deuterium and halogen atoms, carbamoyl, cyano and hydroxy radicals, 1–6C alkyl and alkoxy radicals, and 2 6C alkanoyloxy radicals provided that when A is linked to $R^6$ through a nitrogen atom thereof, it may not bear a hydroxy, alkoxy or alkanoyloxy substituent on the carbon atom adjacent to such nitrogen atoms; and $R^6$ is a 1H-1,2,4-triazol-1-yl or 4H-1,2,4-triazol-4 yl; and the pharmaceutically acceptable acid addition salts thereof.]

[2. A compound as claimed in claim 1 wherein $R^1$ is an azido, carbamoyl, cyano, formyl, hydroxy, nitro, hydroxymethyl, 1-hydroxyethyl, 1-hydroxy-1-methylethyl, 1-hydroxypropyl, 1-hydroxy-1-methylpropyl, 1-hydroxy-2-methylpropyl, 1-hydroxybutyl, 1-hydroxypentyl, 1-hydroxyhexyl, methoxy, ethoxy, propoxy, isopropoxy, butoxy, isobutoxy, sec-butoxy, tert-butoxy, pentyloxy, neopentyloxy, hexyloxy, methylthio, ethylthio, propylthio, isopropylthio, butylthio, isobutylthio, sec-butylthio, tert-butylthio, pentylthio, neopentylthio, hexylthio, methylsulphinyl, ethylsulphinyl, propylsulphinyl, isopropylsulphinyl, butylsulphinyl, isobutylsulphinyl, sec-butylsulphinyl, tert-butylsulphinyl, pentylsulphinyl, neopentylsulphinyl, hexylsulphinyl, methylsulphonyl, ethylsulphonyl, propylsulphonyl, isopropylsulphonyl, butylsulphonyl, isobutylsulphonyl, sec-butylsulphonyl, tert-butylsulphonyl, pentylsulphonyl, neopentylsulphonyl, hexylsulphonyl, acetyl, butyryl, isobutyryl, valeryl, isovaleryl, pivaloyl, hexanoyl, chloroacetyl, dichloroacetyl, trichloroacetyl, trifluoroacetyl, 2,2,2-trichloropropionyl, 2,2,2-trifluoropropionyl, 1,2,2-trifluoropropionyl, 1,2,2,2-tetrafluoropropionyl, perfluoropropionyl, 2,2,3,3,3-pentafluorobutyryl, 2,2-dichloro-3,3,3-trifluorobutyryl, 4,4,4-trifluorovaleryl, 5,5,5-trifluorohexanoyl, acetoxy, propionyloxy, butyryloxy, isobutyryloxy, valeryloxy, isovaleryloxy, pivaloyloxy, hexanoyloxy, acetamido, propionamido, butyramido, isobutyramido, valeramido, isovaleramido, pivalamido, hexanamido, methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl or pentyloxycarbonyl radical; $R^2$ and $R^3$, which may be the same or different, are each a methyl, ethyl, propyl, isopropyl, butyl, isobutyl, sec-butyl, tert-butyl, pentyl, neopentyl, hexyl, trideuteriomethyl, mono-, di or tri-chloromethyl, mono-, di- or trifluoromethyl, 2,2,2-trichloro- or trifluoro-ethyl, 1,2,2-trichloro-or trifluoro-ethyl, pentafluoroethyl, 2,2,3,3,3-pentafluoropropyl, 2,2-dichloro-3,3,3-trifluoropropyl, 4,4,4-trifluorobutyl, 5,5,5-trifluoropentyl or 6,6,6-trifluorohexyl radical, or $R^1R^2R^3C$ is a 1,1-dicyanoethyl or trifluoromethylsulphonyl radical; $R^4$ is a hydrogen atom, a cyano or nitro radical, or a 1–6C alkyl or halogenoalkyl radical as defined above; $R^5$ has any of the values defined above for the group $R^1R^2R^3C$, or has any of the values defined above for $R^4$, or is a 1–6C alkoxy or a 2 6C alkanoyl or alkoxycarbonyl radical as defined above, or a carbamoyl, 1-pyrrolidinylcarbonyl, piperidinocarbonyl, morpholinocarbonyl or nitro radical, a fluorine, chlorine, bromine or iodine atom, or a mono-, di- or tri-chloromethoxy, mono-, di- or trifluoromethoxy, bromomethoxy, iodomethoxy, 2,2,2-trichloro- or trifluoro-ethoxy, 1,2,2-trichloro- or trifluoro-ethoxy, pentafluoroethoxy, 2,2,3,3,3-pentafluoropropoxy, 2,2-dichloro-3,3,3-trifluoropropoxy, 4,4,4-trifluorobutoxy, 5,5,5-trifluoropentyloxy or 6,6,6-trifluorohexyloxy radical; A is an ethylidene, propylidene, butylidene, 1- or 2-methylethylene, 1,2-dimethylethylene, dideuteriomethylene, difluoromethylene, hydroxymethylene, cyanomethylene or carbamoylmethylene radical, or a 1-hydroxyethylene radical (in which C-1 of the ethylene is linked to the benzene ring) radicals.]

[3. A compound as claimed in claim 1 which is a hydrochloride, hydrobromide, sulphate, nitrate, phosphate or toluene-p-sulphonate.]

[4. A compound as claimed in claim 1, 2 or 3 wherein $R^1$ is a carbamoyl, cyano, hydroxy, 1-hydroxyethyl, methylthio, methylsulphinyl, methylsulphonyl or acetyl radical $R^2$ and $R^3$, which may be the same or different, are each a methyl, ethyl, trideuteriomethyl or fluoromethyl radical; $R^4$ is a hydrogen, fluorine or bromine atom or a cyano, nitro, isopropyl or chloromethyl radical; $R^5$ is a 1-cyano-1-methylethyl, 1,1-dimethyl-2-oxopropyl, 1-carbamoyl-1-methylethyl, 1-cyano-1-trideuteriomethyl-2,2,2-trideuterioethyl, 1-cyano-2-fluoro-1-(fluoromethyl)ethyl, 1-methyl-1-(methylsulphonyl)-ethyl, 1-cyano-1-ethylpropyl, carbamoyl, 1-piperidinocarbonyl, 1-morpholinocarbonyl, acetyl or methoxycarbonyl radical; A is a methylene, ethylene, ethylidene, isopropylidene, dideuteriomethylene, hydroxymethylene, cyanomethylene, fluoromethylene or difluoromethylene radical, or a 1-hydroxyethylene radical in which the carbon atom bearing the hydroxy substituent is bonded to the benzene ring; and $R^6$ is a 1H-1,2,4-triazol-1-yl, 4H-1,2,4-triazol-4-yl.]

[5. A compound as claimed in claim 1 wherein $R^1$ is a cyano radical, $R^5$ is a radical of the formula $R^1R^2R^3C$ wherein $R^1$ is a cyano or hydroxy radical, and $R^6$ is a 1 H-1,2,4-triazol-1-yl radical.]

[6. A compound as claimed in claim 5 wherein $R^2$ and $R^3$, both in the group $R^1R^2R^3C$ and in $R^5$, are methyl or trideuteriomethyl radicals, and A is a methylene or dideuteriomethylene radical.]

7. A compound [as claimed in claim 1 which is] *selected from the group consisting of* 2,2'-[5-(1H-1,2,4-triazol-1-ylmethyl)-1,3-phenylene]di(2-methylpropiononitrile), [2-[3-(1-hydroxy-1-methylethyl)-5-(1H-1,2,4-triazol-1-ylmethyl)phenyl]-2-methylpropiononitrile,] 2,2'-[5-dideuterio(1H-1,2,4-triazol-1-yl)-methyl-1,3-phenylene]di(2-trideuteriomethyl-3,3,3-trideuteriopropiononitrile) [or] *and* 2,2'-[5-dideuterio(1H-1,2,4-triazol-1-yl)methyl-1,3-phenylene]di(2-methylpropiononitrile), *or a pharmaceutically acceptable acid addition salt thereof.*

8. A pharmaceutical or veterinary composition which comprises an effective amount of a compound as claimed in claim [1] *7* together with a pharmaceutically or veterinarily acceptable diluent or carrier.

9. A method of treating steroid hormone-dependent tumours which comprises administering to a host in need of such treatment an effective amount of a compound as claimed in claim [1] *7*.

*10. A compound of claim 7 which is 2,2'-[5-(1H-1,2,4-triazol-1-ylmethyl)-1,3-phenylene]di(2-methylpropiononitrile).*

*11. A composition of claim 8 wherein the compound is 2,2'-[5-(1H-1,2,4-triazol-1-ylmethyl)1,3-phenylene]di(2-methylpropiononitrile).*

*12. The method of claim 9 wherein the compound is 2,2'-[5-(1H-1,2,4-triazol-1-ylmethyl)1,3-phenylene]di(2-methylpropiononitrile).*

*13. A compound of claim 7 which is 2,2'-[5-dideuterio (1H-1,2,4-triazol-1-yl)methyl-1,3-phenylene]di(2-trideuteriomethyl-3,3,3-trideuteriopropiononitrile).*

*14. A compound of claim 7 which is 2,2'-[5-dideuterio (1H-1,2,4-triazol-1-yl)methyl-1,3-phenylene]di(2-methylpropiononitrile).*

*15. A compound as claimed in claim 7 which is a hydrocholoride, hydrobromide, sulphate, nitrate, phosphate or toluene-p-sulphonate.*

*16. A compound selected from the group consisting of 2,2'-5-(1H-1,2,4-triazol-1-ylmethyl)-1,3-phenylene]di(2-methylpropiononitrile), 2,2'-[5-dideuterio(1H-1,2,4-triazol-1-yl)methyl-1,3-phenylene]di(2-trideuteriomethyl-3,3,3-trideuteriopropiononitrile) and 2,2'-[5-dideuterio(1H-1,2,4-triazol-1-yl)methyl-1,3-phenylene]di(2-methylpropiononitrile).*

* * * * *